US006936458B1

(12) United States Patent
Anders et al.

(10) Patent No.: US 6,936,458 B1
(45) Date of Patent: Aug. 30, 2005

(54) ISOLATED DNA COMPRISING ONE OR MORE GENES SPECIFIC FOR 5S CLAVAM BIOSYNTHESIS, VECTORS COMPRISING SUCH DNA AND STREPTOMYCES HOSTS CAPABLE OF IMPROVED CLAVULANIC ACID PRODUCTION

(75) Inventors: Cecilia Anders, Edmonton (CA); Barry Barton, Worthing (GB); John Patrick Griffin, Worthing (GB); Susan Jensen, Edmonton (CA); Roy Henry Mosher, Staten Island, NY (US); Ashish Sudhakar Paradkar, San Diego, CA (US)

(73) Assignees: SmithKline Beecham p.l.c., Brentford (GB); The Governors of the University of Alberta, Alberta (CA)

( * ) Notice: Subject to any disclaimer, the term of this patent is extended or adjusted under 35 U.S.C. 154(b) by 0 days.

(21) Appl. No.: 09/350,702

(22) Filed: Jul. 9, 1999

Related U.S. Application Data

(63) Continuation of application No. 09/018,806, filed on Feb. 4, 1998, now abandoned.

(30) Foreign Application Priority Data

Feb. 4, 1997 (GB) .............................................. 9702218

(51) Int. Cl.$^7$ ............................. C12N 1/21; C12N 9/00; C12N 15/52; C07H 21/04
(52) U.S. Cl. .............................. 435/252.35; 435/252.3; 435/320.1; 536/23.2
(58) Field of Search ......................... 435/252.3, 252.35, 435/320.1, 240; 536/23.2, 23.7

(56) References Cited

U.S. PATENT DOCUMENTS 4,202,819 A    5/1980   Kellett et al. ............... 540/347

FOREIGN PATENT DOCUMENTS

| CA | 2.108.113 | 4/1995 |
| ES | 550549 | 3/1987 |
| GB | 1 585 661 | 3/1981 |
| JP | 53-104796 | 9/1978 |

OTHER PUBLICATIONS

Hodgson, J.E. et al., Gene, (1995) vol. 166, pp. 49–55.
Egan, L.A. et al., J AM. Chem. Soc., (1997), vol. 119, pp. 2348–2355.
Busby, R.W., J. Biological Chem., (1995), vol. 270(9), pp. 4262–4269.
Brown, D. et al., J.C.S. Chem. Comm., (1979), pp. 282–283.
Evans, R. H. et al., J. Antiobiotics, (1983), vol. 36(3), pp. 213–216.
Muller, J–C. et al, J. Antiobiotics, (1983), vol. 36(3), pp. 216–224.
Marsh, E.N. et al., Biochemistry, (1992), vol. 31, pp. 12648–12657.
King, H.D. et al., J. Antiobiotics, (1986), vol. 39(4), pp. 510–515.
Janc, J.W. et al., J. Biological Chem., (1995), vol. 270(10), pp. 5399–5404.
Iwata–Reuly, D. and C. A. Townsend, J. Am. Chem. Soc., (1992), vol. 114, pp. 2762–2763.
Paradkar, A. S. and S. E. Jensen, J. Bacteriology, (1995), vol. 177(5), pp. 1307–1314.
Baldwin, J. E. et al., Tetrahedron Letters, (1994), vol. 35(17), pp. 2783–2786.
A.L. Demain, "Biosynthesis and Regulation of Beta–Lactam Antibiotics", In: 50 Years of Penicillin Applications, History & Trends (1990).
Townsend, et al., J. Am. Chem. Soc., 107(4):1066–1068 (1985).
Valentine, et al., J. Chem. Soc. Chem. Comm., 15:1210–1211 (1993).
Jane, et al., Bioorg. Med. Chem. Lett., 3:2313–2316 (1993).
Rohl, et al., Arch. Microbiol., 147:315–320 (1987).
Aidoo, et al., Gene, 147:41–46 (1994).
Sambrook, et al., Molecular Cloning: A Laboratory Manual, 2nd Edition. Cold Spring Harbor Laboratory, Cold Spring Harbor, NY (1989).
British Pharmacopoeia (1993); Addendum (1994) pp. 1362–1363.
British Pharmacopoeia Official Monographs, USP 23 NF18 pp: 384–385 (1985).
Hopwood, et al., Genetic Manipulation of Streptomyces. A Cloning Manual (1985).
Stahl, et al., In: Nucleic Acid Techniques in Bacterial Systematics. Ed. E. Stackebrandt & M. Goodfellow. Toronto: John Wiley & Sons, pp. 204–248 (1991).
Doran, et al., J. Bacteriol., 172(9):4909–4918 (1990).
Vieira, et al., Methods Enzymol., 153: 3–11 (1987).
Sanger, et al., Proc. Natl. Acad. Sci. USA, 74: 5463–5467 (1977).
Ward, et al., Mol. Gen. Genet. 203: 468–478 (1986).
Preuss, et al., The Journal of Antibiotics, XXXVI(3): 208–212 (1983).
Bailey, et al., "Cloning a *Streptomyces clavuligerus* Genetic Locus Involved in Clavulanic Acid Biosynthesis". *Biotechnology*, Sep. 1984.
Jensen, et al., "Extending the β–Lactam Biosynthetic Gene Cluster in *Streptomyces clavuligerus*". *Industrial Microorganisms—Basic and Applied Molecular Genetics*, Chapter 22, pp. 169–176 (1993).
Mosher, et al., "Genes Specific for the Biosynthesis of Clavam Metabolites Antipodal to Clavulanic Acid are Clustered with the Gene for Clavaminate Synthase 1 in *Streptomyces clavuligerus*", Antimicrobial Agents and Chemotherapy, 43(5): 1215–1224 (1999).

Primary Examiner—Elizabeth Slobodyansky
(74) Attorney, Agent, or Firm—Andrea V. Lockenour; Jeffrey A. Sutton

(57) ABSTRACT

Novel bacterial genes, microorganisms and processes for improving the manufacture of 5R clavams, eg. clavulanic acid.

23 Claims, 17 Drawing Sheets

Figure 1: Nucleotide sequence of the *S. clavuligerus* chromosome
including and flanking *cas1*

```
      NcoI
   1
GGTACCGCCCGCCGCCGACGGGGCCTCGGAGCCGGCCTGGCCACTGGTCCTGGTGGGGCC    60
         M  A  P  P  P  Q  G  P  A  E  A  P  G  T  V  L  V  V  G

61
ACCCTATCACCGGGCGGTGGGCCGCGTCGTCTGAGGGCCTGTGCCTGGGCACCCACACGC   120
      T  P  Y  H  G  A  V  R  R  L  L  S  G  S  V  S  G  H  T  H

<orfup3
```

```
    121
GCCTTTCCGGGCCTCCGGCCCAGTGTCGGTGCCCATTGCGCGCCACAGGAACGGGCGCAT   180
              *  L  W  P  Y  R  A  T  D  K  G  A
 Y
         A  S  L  G  P  P  R  T  M

181
TAGCCCCAGGTCTATCTGCTTCCGGGCCACCTGCTCCTTCAGGGCGTGGAGCATCTGGCA   240
         D  P  D  L  Y  V  F  A  R  H  V  L  F  D  R  V  E  Y  V
 T

241
CGTGGTCGCGGGCCGCCGGGTGAGCCCCAGTGGGCGGGCGGTGCCGGGCAGGGCCACGAG   300
            C  W  R  G  A  A  W  E  P  D  G  A  R  W  P  G  D  R  H
 E

301
TGGCACCCACCACGGGAGGCGCCGCTCCTCAAGCCAGGGCCAGTCTTAGGTCAACTGCCT   360
            G  H  T  T  G  E  A  A  L  L  E  T  G  T  L  I  W  N  V
 S

361
GGTGTCTACCACCCACTAGCTCGCCTACCACGGGGGCTCCAGCAGCTTCTCGGCCCGCTA   420
            W  L  H  H  T  I  S  R  I  T  G  G  L  D  D  F  L  R  A
 I

421
GAGCCTGAACGGGGCCCGGTCTGGGGTGAACCCCTTCTTCTTCTGGCGCAGGAGCCGCTT   480
            E  S  K  G  R  A  L  G  W  K  P  F  F  F  V  A  D  E  A
 F

481
CATCAGCTAGCGCCCCCACGGCAGCGACGGCTGCGGCGGCAACAGCTTGCGGAACTTCAT   540
            Y  D  I  A  P  T  G  D  S  G  V  G  G  N  D  F  A  K  F
 Y
```

541
GCGCCACTACTGGCGGAACGCGACGAGCAGGCAGTATGGCCGGCTACGGTGCCTGTACTT    600
      A  T  I  V  A  K  R  Q  E  D  T  M  G  A  S  A  V  S  M

601
TGCTGGAGGTCTCTAAGGCCCACCGACACGACCCCGACGCCTTCCCCACAGGGGGCGCTT    660

661
CCTGCCGCCTGCGGCGCCTGCGGCGCCGGCAGAGGGGCCGCCTGCCCAGGGTCGCAGGAC    720

721
CTCTCCCGAACCGCCGCCGAACTGCGGCACGACAGGGCGCCGAACGCCTTGCGCTTCATG    780

781
GCCGGTCGCATGCCCGCAACGTGGCCTGCACATGCGGCCAGCCCTGGGGAGCATGGGGGC    840

841
CTCGGCCGGCTGGGGCCGCCGAGGCCCCCATGCCTGCGCGGCCTGGCCGGGCTCGCTCGG    900

901
CCTGCCCAGCCTGCCACGCGCACCAAGGCCACACAGCCTGTCGAGCCTGCCTGGCCTGCC    960

961
ACGCGCACCAAGGCCACACAGCCTGTCGAGCCTGCCCAGCCTGCCACGCGCACCAAGGCC    1020

1021
GTGCGGCCTGCCCAGTCAACGGCTAGTACCGCTCGTTACGGCCCCACATGGCGAGGGGCC    1080
                    *  N  G  I  M  A  L  L  A  P  T  Y  R  E  G

1081
TGTGGCCCACCCTCTAGCGCCGGCAGTGGAGGCGCTCCCTGGCCAGCAGGTCGGCCTAGC    1140
  S  V  P  H  S  I  A  A  T  V  E  A  L  S  R  D  D  L  R  I

1141
TCCGCCGCCGCTCTAACAGGCGCTCTACCCGGCCCAAGCGCCACGGGCCCTAGCCCTGCT    1200

```
          S  A  A  A  L  N  D  A  L  H  A  P  N  A  T  G  P  I  P  V

1201
GCAGGAGCGGGGCCACCACGTCGGTCCGCTCGCGCTCGACACGGTCCCAGTCGGGGTCTG  1260
       V  D  E  G  R  H  H  L  W  A  L  A  L  Q  A  L  T  L  G  L

1261
GCAGGCGCTGGCCCGCGTCGGCCACGTCGTTGCTCGCCAACGCGCGCTCCCGGCCTCGCG  1320
        G  D  A  V  P  R  L  R  H  L  L  S  R  N  R  A  L  A  P  A

1321
ACTTGGCCCCGACCGGGGCCGCCTTCAGGAGCAGGGGGTCTAGCAGCCACCACGCCTACC  1380
       S  F  R  P  Q  G  R  R  F  D  E  D  G  L  D  D  T  T  R  I

1381
ACGGCCACTCTTTTGGGGCAGGGTCTCCCCGCATTCGCTGCTAGGGCTAGGGGTCGAGGG  1440
         T  G  T  L  F  G  R  G  L  P  A  Y  A  V  I  G  I  G  L  E

1441
CCGTCTGCCCGTGGTGGAGCAGGAGCTAGGGCGCGCTGGTGTCCGAGGTGAGCGAGACGT  1500
       R  C  V  P  V  V  E  D  E  I  G  R  S  W  L  S  W  E  S  Q

1501
GGCGGCAGTGGCCCACGTGGCGCAGGCGGGCCGCGTCGCACCGGCGCCTCCCGAGCCTCT  1560
       V  A  T  V  P  H  V  A  D  A  R  R  L  T  A  A  S  P  E  S

1561
CTGGCTCGGACGCCTGGAACGGGAGCGCGTGGTCGAGCCGGTGGCGTGGGTGCCAGAGGA  1620
         L  G  L  R  R  V  K  G  E  R  V  L  E  A  V  A  G  V  T  E

1621
GCTAGCCGTGGCGGCCCAGGCAGGTCACGACCATCATGTCCAGCTACGCCAGCCACGGCT  1680
        E  I  P  V  A  P  D  T  W  H  Q  Y  Y  L  D  I  R  D  T  G

1681
CTGCTGCGTCCCTGGCAAGCGTCCGGCGCGCCTGCATCCTGCCGAGCGGCGTGTTCGGGA  1740
```

```
              L  R  R  L  S  R  E  C  A  A  R  V  Y  S  P  E  G  C  L  G

1741
    CCCTCCGCGGCAGCCTGCTCGCGTGGTACGGCTTGAACCACCGCTAGTCGTGGAGCAGGG    1800
           Q  S  A  G  D  S  S  R  V  M  G  F  K  T  A  I  L  V  E  D

1801
    CCGCCGGGCGCTGGCGGGCAGGCTCGTCGAGGAGTGGCCGCGGCTCGGGGACCTGCAGCC    1860
           R  R  G  A  V  A  R  G  L  L  E  E  G  A  G  L  G  Q  V  D

1861
    GCCACAGGTCGTCCCACTGGGGCCGCAGCTGCCGCCGCGCCTACCACCGGCAGCGGGCCC    1920
           A  T  D  L  L  T  V  G  A  D  V  A  A  R  I  T  A  T  A  R

1921
    GCGCCAGGCCCGCAGGCATCTTCAGCCACCAGCCGTCCGTCGGCTCGGGGACCCGTGACT    1980
           A  R  D  P  R  G  Y  F  D  T  T  P  L  C  G  L  G  Q  A  S

1981
    GGCCTTCCAGGGCGTCCCGCGCCTGGCCGCCTGCGCCTTGGCGCCGCCTGTGCCTTGGCC    2040
           V  P  L  D  R  L  A  R  V  P  P  R  P  V  A  A  S  V  S  G

<orfup1
    2041
    CCGGGGACTCGGGCGGAGAGCGGGACATACGGAACCTCCACAGGCGGAGCCGGGAACGGG    2100

GGCCCCTGAGCCCGCCTCTCGCCCTGTATGCCTTGGAGGTGTCCGCCTCGGCCCTTGCCC
           A  P  S  E  P  P  S  R  S  M

2101
    ACGAGGGCGAGGACGGGACGGAACGAAGGAGAGGACGGGACGGACAGCACGGACGGGACG    2160

TGCTCCCGCTCCTGCCCTGCCTTGCTTCCTCTCCTGCCCTGCCTGTCGTGCCTGCCCTGC

2161
    GACGGAACGGAGTCGGGAACCGGGGGGGGTGACCGGAACCGGGCCGTCCTTGGCCCTCCC    2220
```

```
CTGCCTTGCCTCAGCCCTTGGCCCCCCCCACTGGCCTTGGCCCGGCAGGAACCGGGAGGG

2221
CCGTCCTCCCCGCCATCCGCCGTTCTCCCCCGTTCCCTCTCCCGTCCTCCAGCCAACACC    2280

GGCAGGAGGGGCGGTAGGCGGCAAGAGGGGGCAAGGGAGAGGGCAGGAGGTCGGTTGTGG

2281
GCCGCCCTTTCCAAGCGCTTGACACGGCACCGACAGCCGCCGCCGGGCGCCCGATGGGGA    2340

CGGCGGGAAAGGTTCGCGAACTGTGCCGTGGCTGTCGGCGGCGGCCCGCGGGCTACCCCT

2341
CCCGTGCCCGCCGGTGAGCGGCGGTGAGCGCCGGTACGGGACCCCACGCGCCGCCGCCCG    2400

GGGCACGGGCGGCCACTCGCCGCCACTCGCGGCCATGCCCTGGGGTGCGCGGCGGCGGGC

2401
GGCGCCCGCCAGGGCCCGCGCGGCCACCCCGGCCCGCCCCGGCCGGAGCGGCGATCCGGG    2460

CCGCGGGCGGTCCCGGGCGCGCCGGTGGGGCCGGGCGGGGCCGGCCTCGCCGCTAGGCCC

2461
CCGCTCGCTGCAAGAGGAACATCCACAGCCGCACAAGGAGCGCTCCGCACAGTGGGCACC    2520

GGCGAGCGACGTTCTCCTTGTAGGTGTCGGCGTGTTCCTCGCGAGGCGTGTCACCCGTGG

2521
ACGTCCGCCCCGTCCCCCACACCGTGGCCGGTCCCCACCGGACAGCACAGCACCGCACAG    2580

TGCAGGCGGGGCAGGGGGTGTGGCACCGGCCAGGGGTGGCCTGTCGTGTCGTGGCGTGTC

2581
CACCACATCGCACGGCACAGCACAGCACCACCGGCACGAGGAACCAAGGAAAGGAACCAC    2640

GTGGTGTAGCGTGCCGTGTCGTGTCGTGGTGGCCGTGCTCCTTGGTTCCTTTCCTTGGTG
```

```
                    cas1>
                M  T  S  V  D  C  T  A  Y  G  P  E  L  R  A  L  A  A
     2641
ACCACCATGACCTCAGTGGACTGCACCGCGTACGGCCCCGAGCTGCGCGCGCTCGCCGCC    2700

TGGTGGTACTGGAGTCACCTGACGTGGCGCATGCCGGGGCTCGACGCGCGCGAGCGGCGG

2701
CGGCTGCCCCGGACCCCCCGGGCCGACCTGTACGCCTTCCTGGACGCCGCGCACACAGCC   2760
        R  L  P  R  T  P  R  A  D  L  Y  A  F  L  D  A  A  H  T  A

2761
GCCGCCTCGCTCCCCGGCGCCCTCGCCACCGCGCTGGACACCTTCAACGCCGAGGGCAGC   2820
        A  A  S  L  P  G  A  L  A  T  A  L  D  T  F  N  A  E  G  S

2821
GAGGACGGCCATCTGCTGCTGCGCGGCCTCCCGGTGGAGGCCGACGCCGACCTCCCCACC   2880
        E  D  G  H  L  L  L  R  G  L  P  V  E  A  D  A  D  L  P  T

NcoI

2881
ACCCCGAGCAGCACCCCGGCGCCCGAGGACCGCTCCCTGCTGACCATGGAGGCCATGCTC   2940
        T  P  S  S  T  P  A  P  E  D  R  S  L  L  T  M  E  A  M  L

KpnI

2941
GGACTGGTGGGCCGCCGGCTCGGTCTGCACACGGGGTACCGGGAGCTGCGCTCGGGCACG   3000
        G  L  V  G  R  R  L  G  L  H  T  G  Y  R  E  L  R  S  G  T

3001
GTCTACCACGACGTGTACCCGTCGCCCGGCGCGCACCACCTGTCCTCGGAGACCTCCGAG   3060
        V  Y  H  D  V  Y  P  S  P  G  A  H  H  L  S  S  E  T  S  E

3061
ACGCTGCTGGAGTTCCACACGGAGATGGCCTACCACCGGCTCCAGCCGAACTACGTCATG   3120
        T  L  L  E  F  H  T  E  M  A  Y  H  R  L  Q  P  N  Y  V  M
```

```
3121
CTGGCCTGCTCCCGGGCCGACCACGAGCGCACGGCGGCCACACTCGTCGCCTCGGTCCGC  3180
      L  A  C  S  R  A  D  H  E  R  T  A  A  T  L  V  A  S  V  R

3181
AAGGCGCTGCCCCTGCTGGACGAGAGGACCCGGGCCCGGCTCCTCGACCGGAGGATGCCC  3240
   K  A  L  P  L  L  D  E  R  T  R  A  R  L  L  D  R  R  M  P

3241
TGCTGCGTGGATGTGGCCTTCCGCGGCGGGGTGGACGACCCGGGCGCCATCGCCCAGGTC  3300
      C  C  V  D  V  A  F  R  G  G  V  D  D  P  G  A  I  A  Q  V

3301
AAACCGCTCTACGGGGACGCGGACGATCCCTTCCTCGGGTACGACCGCGAGCTGCTGGCG  3360
    K  P  L  Y  G  D  A  D  D  P  F  L  G  Y  D  R  E  L  L  A

3361
CCGGAGGACCCCGCGGACAAGGAGGCCGTCGCCGCCCTGTCCAAGGCGCTCGACGAGGTC  3420
       P  E  D  P  A  D  K  E  A  V  A  A  L  S  K  A  L  D  E  V

3421
ACGGAGGCGGTGTATCTGGAGCCCGGCGATCTGCTGATCGTCGACAACTTCCGCACCACG  3480
      T  E  A  V  Y  L  E  P  G  D  L  L  I  V  D  N  F  R  T  T

3481
CACGCGCGGACGCCGTTCTCGCCCCGCTGGGACGGGAAGGACCGCTGGCTGCACCGCGTC  3540
         H  A  R  T  P  F  S  P  R  W  D  G  K  D  R  W  L  H  R  V

3541
TACATCCGCACCGACCGCAATGGACAGCTCTCCGGCGGCGAGCGCGCGGGCGACGTCGTC  3600
         Y  I  R  T  D  R  N  G  Q  L  S  G  G  E  R  A  G  D  V  V

A  F  T  P  R  G  *  SacI

3601
GCCTTCACACCGCGCGGCTGAGCTCCCGGGTCCGACACCGCGCGGCTGAACCCACGGTCC  3660

CGGAAGTGTGGCGCGCCGACTCGAGGGCCCAGGCTGTGGCGCGCCGACTTGGGTGCCAGG
```

```
     3661
GGGGCCCACGGTCCGGCACCGCGCGGCTGAGCCCCCGGGTCCGGCAGCGGGCGGCTGAAC    3720

CCCCGGGTGCCAGGCCGTGGCGCGCCGACTCGGGGGCCCAGGCCGTCGCCCGCCGACTTG

3721
CCCCGCCCCGGGCCACCGCCCGACCGCCCCCGCGCACCGGACGCGCCCGCCTGTACGGCG    3780

GGGGCGGGGCCCGGTGGCGGGCTGGCGGGGGCGCGTGGCCTGCGCGGGCGGACATGCCGC

3781
GTCCCGCCCGGGCCCGTACACCTGAAGCGCCCGGCGGACCGCCGCCCCGCCGGGGGACGG    3840

CAGGGCGGGCCCGGGCATGTGGACTTCGCGGGCCGCCTGGCGGCGGGGCGGCCCCCTGCC

--------------->    <-------------------

3841
ACAGAGCCGGGTGCGGGAGGACGTCCTCCCGCACCCGGCTCCCACCGTTCCGCACCGACC    3900

TGTCTCGGCCCACGCCCTCCTGCAGGAGGGCGTGGGCCGAGGGTGGCAAGGCGTGGCTGG

3901
GCACCCGACCGTGCCGCAGGCGCCACCGGCACCGCACCGCCCGCGCCGGCAGCCACCACA    3960

CGTGGGCTGGCACGGCGTCCGCGGTGGCCGTGGCGTGGCGGGCGCGGCCGTCGGTGGTGT

3961
GGCGCCACGCCGCCCGCACGGTGCCCGCGCTGCTCAGCCCCCGTCCACCGGGCTGTCCAG    4020

CCGCGGTGCGGCGGGCGTGCCACGGGCGCGACGAGTCGGGGGCAGGTGGCCCGACAGGTC
                                             *  G  G  D  V  P  S  D
L

4021
GTCGGCGGCGTCGCGCGGGGGCTACTTGAGGGCCAGCCGCCGGCTGGGGGGCCTGGGGCG    4080
         L  R  R  L  A  G  G  I  P  E  R  D  A  A  S  G  G  S  G
A
```

```
   4081
CTCTACGGGGGTGTGAGGGCCCTAGTGGAGGTCGCTCCGTATGCCGTCGTCTAGCCGGTG    4140
        L  H  G  W  V  G  P  I  V  E  L  S  A  Y  P  L  L  D  A
V

4141
GGCGAAGAGCAGGAGCTGCCGCTTTGTGTGCAGGTCCCGCGGGCCGTCGTGGTGCCGGGC    4200
        R  K  E  D  E  V  A  F  C  V  D  L  A  G  P  L  V  V  A
R

4201
GCGGCACTGCCTCCGGTCGCGGCGGAGCTGCGAGGGGGGCCGGGGCCCACAGCGGGGGTG    4260
        A  T  V  S  A  L  A  A  E  V  S  G  G  A  G  P  T  A  G
V

NcoI
   4261
TAGGCACAAGAGGGTCCACGCGTGGTACCACTCGTCTAGGCGCCGCGGCCCGGGCCTCTC    4320
        D  T  N  E  W  T  R  V  M  T  L  L  D  A  A  G  P  G  S
L

4321
CTTCTGGACGAGGGTCTTCGGCCACTCCATGAGGAGCGCCCACCGCTTTGGGTCGAGGGC    4380
        F  V  Q  E  W  F  G  T  L  Y  E  E  R  T  A  F  G  L  E
R

4381
CACCCGTGCCGCCCGGGTCTTCCTTGCGCTCCAGGGGGTGGGCCGCTTGTGGGCCGGGCG    4440
        H  A  R  R  A  W  F  S  R  S  T  G  W  G  A  F  V  R  G
A

4441
GCGGAAGGCGGGGGCGAGGGGCCGCAGCCGCGACTCGCGGCGCCGGTCTGGCCTGTCGTC    4500
        A  K  R  G  R  E  G  A  D  A  S  L  A  A  A  L  G  S  L
L
```

```
   4501
CTGGTCCGACACGCCCGACGAGTGGCCGCGGGGCGTCTAGCCCCGCTAGGCCGCGTGGTA    4560
      V  L  S  H  P  S  S  V  P  A  G  C  I  P  A  I  R  R  V
M

4561
GGGGCCTACGCTGTGCCGGGTGACCATCCGCACCCGGCGCGGGTAGCTGGTCGGGCACTG    4620
      G  P  H  S  V  A  W  Q  Y  A  H  A  A  G  M  S  W  G  T
V

4621
GTCCCGGTCAAGGGCATGGGGGTCGAGGAGCCACTCGTCGGCCACGACGCGGCGCTGTAA    4680
      L  A  L  E  R  V  G  L  E  E  T  L  L  R  H  Q  A  A  V
N

4681
CAGGACGCCTCACTAGTCGCCTTTCGCCCTGGGGCTGCCCACCAACGGCCCGCTCGACCT    4740
      D  Q  P  T  I  L  P  F  R  S  G  S  P  H  N  G  P  S  S
S

4741
CTGGGGCAACGGCTTCTCAGGCCGCCACTGCTGCGTCATGGCGGCCCACAGGTCGCCGTC    4800
      V  G  N  G  F  L  G  A  T  V  V  C  Y  R  R  T  D  L  P
L

4801
GGGGCGTGGCTAGTCGGTCAGCATGGGCCACACCAGGGCCGGCTTCTTGCTGCCTGTCTC    4860
      G  A  G  I  L  W  D  Y  G  T  H  D  R  G  F  F  S  P  C
L

4861
GTGGTGCAAGCAGGGCAGCCGCAAGCCGCACGGCATGTACCGCATTGGCTAGGCCCGCAG    4920
      V  V  N  T  G  D  A  N  P  T  G  Y  M  A  Y  G  I  R  A
D

<orfdwn1
   4921
GGCGTCCTGGAGGGGCAGGTCGTTGCCGTCAAGCAGCTAGAGCTTATACGCCGTAAGGTG    4980
```

```
                  R  L  V  E  G  D  L  L  P  L  E  D  I  E  F  I  R  C  E
      M
      4981
      GCGACTGGAGGAACAAGCTAGGGGGGCCTGTTGTCCAGCCAGCACCGGCCTCTGAGTCTC    5040
      L

5041
      GGTCAACCCCCGCTAGAGCCACCGGGTGTCGAGGTCCGACGCGTCGACCTGTAGCACGCC    5100
                 W  N  P  A  I  E  T  A  W  L  E  L  S  R  L  Q  V  D  H
      P

5101
      CTAGTCGGGCCTCATGACCGTGACCTCGTCTATGAGGCCTAGCACGGCGAGGTGGTCGAA    5160
            I  L  G  S  Y  Q  C  Q  L  L  Y  E  P  D  H  R  E  V  L
      K

5161
      GAGCTAGTACGCCAACTACAGCAGGCCCCACGGCTGGGTGAGGTCGGGGGCCAGCTGGTC    5220
            E  I  M  R  N  I  D  D  P  T  G  V  W  E  L  G  R  D  V
      L

5221
      CCAGAACATCAGGCTCGGCTAGCCTGGGCAGAGCGGCCAGCGCGCGTCGCGGAGCCACTT    5280
            T  K  Y  D  S  G  I  P  G  T  E  G  T  A  R  L  A  E  T
      F

NcoI
      5281
      CGGGTACCCCGGCTTGGTCAAGAGCTTCTACTTCGGCGGCGGCGCCCTGCGGGTCACCAC    5340
            G  M  P  G  F  W  N  E  F  I  F  G  G  G  R  S  A  W  H
      H

5341
      CCGGAGCGGCCTCAGGGCCCTCTGGTCCTGCAGGAAGTAGTGGGGCTGGGCGAGCGGGGC    5400
            A  E  G  S  D  R  S  V  L  V  D  K  M  V  G  V  R  E  G
      R
```

```
5401
GGCGTCCCACGGCACCGGGCGGCGGAGCCGGAGGAGGGCCATCTACAGGTAGTCGGCCCG   5460
         R  L  T  G  H  G  A  A  E  A  E  E  R  Y  I  D  M  L  R
A

5461
CTGCTAGACCAGCAGCCACAAGTAGTCCTAGCCGTGGTGCGGGAGGGCCCGTGTCTTGGC   5520
         V  I  Q  D  D  T  N  M  L  I  P  V  V  G  E  R  A  C  F
R

5521
CTTGCACAGGAGTGACTTCGACTTGCCGACCTTCTGCCCGCCCACCCCCGCGACCATCCC   5580
         F  T  D  E  S  F  S  F  P  Q  F  V  P  P  H  P  R  Q  Y
P

5581
GAACCCGCGCTACGGGTGGAGCGCCTACTGCGGCAAGAGCAGCTCCGGGGCCGGCATCGC   5640
         K  P  A  I  G  V  E  R  I  V  G  N  E  D  L  G  R  G  Y
R

5641
CGCGTGGCGGAGCATCCCCTTGAGGTCCAGGCCGTGGCCCTAGCAGGTGACGAGGGGCCT   5700
         R  V  A  E  Y  P  F  E  L  D  P  V  P  I  T  W  Q  E  G
S

5701
CACCCACTTGCAGAGCCAGCAGGTGCGGAAGAACTACTAGAGGGTCACGAGGAGCTTCTC   5760
         H  T  F  T  E  T  T  W  A  K  K  I  I  E  W  H  E  E  F
L

5761
CCGTGCTAACGCGGCCAGGGCGAGGGGCCGCAGCCTGTCCCACGGCGGCTGGGGCATGTG   5820
         A  R  N  R  R  D  R  E  G  A  D  S  L  T  G  G  V  G  Y
V
```

```
5821
GACGGGGTACTACAGCCGGGTCGCGAAGACCTTGGGCGCGCGCTAGGGCTGCTTCCGCGC    5880
      Q  G  M  I  D  A  W  R  K  Q  F  G  R  A  I  G  V  F  A
R

5881
CGGGGCCCAGTACACCAGCTCGTAGCGGTCTAGGAGCCGGTCGGCGTCGCCTAACACGTC    5940
      G  R  T  M  H  D  L  M  A  L  D  E  A  L  R  L  P  N  H
L

5941
GCCGTCCTGCAACCGGTAGACCGGCTGGGCCTACACGGCCCAGACGTACGGCTCCATCTC    6000
      P  L  V  N  A  M  Q  G  V  R  I  H  R  T  Q  M  G  L  Y
L

6001
GGGGTCGTACTAGCCCAACAACCTCTGGAGCTTTGGGAGCCACACCTTCACCACGAGCCA    6060
      G  L  M  I  P  N  N  S  V  E  F  G  E  T  H  F  H  H  E
T

6061
CTTCCTGTCAGGGGTCATCGGCTCAAGCAGCCGGCGGACGCGGACGGCCCACTCGACGGC    6120
      F  S  L  G  W  Y  G  L  E  D  A  A  Q  A  Q  R  T  L  Q
R

6121
CTCGTACAAGACCATCAAGACGCCTAACTGGGGGCGGTATGGGGCGACCTGGACGCGTAC    6180
      L  M  N  Q  Y  N  Q  P  N  V  G  A  M  G  R  Q  V  Q  A
H

<orfdwn2

6181
ACTGCCGACCGTTGGCAGATAGAAGAGAATGGACTTCACCCTGGCTCCTCCGGTTCGCGG    6240

TGACGGCTGGCAACCGTCTATCTTCTCTTACCTGAAGTGGGACCGAGGAGGCCAAGCGCC
      S  G  V  T  P  L  Y  F  L  I  S  K  M
```

```
6241
CGCCCTCCATTGACGTGCGCCGAAAGCGGCTCGACCGTCCCACTCCGCCCTTGAGTTCCG   6300
GCGGGAGGTAACTGCACGCGGCTTTCGCCGAGCTGGCAGGGTGAGGCGGGAACTCAAGGC

6301
TCTGACGCCGCGCCAGTCGGCGGGCCGTCCGCCGGGGTGCCCGCCGGGGTCCGCACCCGC   6360
AGACTGCGGCGCGGTCAGCCGCCCGGCAGGCGGCCCCACGGGCGGCCCCAGGCGTGGGCG

6361
CGGACGGCACGGCGCGCACCGCGCGCGCGGCGCTTCGGGGCACCGGGCTCGACGGGGTGC   6420
GCCTGCCGTGCCGCGCGTGGCGCGCGCGCCGCGAAGCCCCGTGGCCCGAGCTGCCCCACG

6421
TCAGCGGGACGTCCAACGGAAGGCAAGCCCCCGTACCCAGCCTGGTCAAGGCGCTCATCG   6480
AGTCGCCCTGCAGGTTGCCTTCCGTTCGGGGGCATGGGTCGGACCAGTTCCGCGAGTAGC
                                                        orfdwn3>
                                                          M  P
G
6481
CCATTCCCTGAGGAGGTCCCGCCTTGACCACAGCAATCTCCGCGCTCCCGACCGTGCCCG   6540
GGTAAGGGACTCCTCCAGGGCGGAACTGGTGTCGTTAGAGGCGCGAGGGCTGGCACGGGC 6541
GCTCCGGACTCGAAGCACTGGACCGTGCCACCCTCATCCACCCCACCCTCTCCGGAAACA   6600
   S  G  L  E  A  L  D  R  A  T  L  I  H  P  T  L  S  G  N
T 6601
CCGCGGAACGGATCGTGCTGACCTCGGGGTCCGGCAGCCGGGTCCGCGACACCGACGGCC   6660
   A  E  R  I  V  L  T  S  G  S  G  S  R  V  R  D  T  D  G
R
```

```
6661
GGGAGTACCTGGACGCGAGCGCCGTCCTCGGGGTGACCCAGGTGGGCCACGGCCGGGCCG  6720
    E  Y  L  D  A  S  A  V  L  G  V  T  Q  V  G  H  G  R  A
E

6721
AGCTGGCCCGGGTCGCGGCCGAGCAGATGGCCCGGCTGGAGTACTTCCACACCTGGGGGA  6780
    L  A  R  V  A  A  E  Q  M  A  R  L  E  Y  F  H  T  W  G
T

6781
CGATCAGCAACGACCGGGCGGTGGAGCTGGCGGCACGGCTGGTGGGGCTGAGCCCGGAGC  6840
    I  S  N  D  R  A  V  E  L  A  A  R  L  V  G  L  S  P  E
P

6841
CGCTGACCCGCGTCTACTTCACCAGCGGCGGGGCCGAGGGCAACGAGATCGCCCTGCGGA  6900
    L  T  R  V  Y  F  T  S  G  G  A  E  G  N  E  I  A  L  R
M

6901
TGGCCCGGCTCTACCACCACCGGCGCGGGGAGTCCGCCCGTACCTGGATACTCTCCCGCC  6960
    A  R  L  Y  H  H  R  R  G  E  S  A  R  T  W  I  L  S  R
R

6961
GGTCGGCCTACCACGGCGTCGGATACGGCAGCGGCGGCGTCACCGGCTTCCCCGCCTACC  7020
    S  A  Y  H  G  V  G  Y  G  S  G  G  V  T  G  F  P  A  Y
H

7021
ACCAGGGCTTCGGCCCCTCCCTCCCGGACGTCGACTTCCTGACCCCGCCGCAGCCCTACC  7080
    Q  G  F  G  P  S  L  P  D  V  D  F  L  T  P  P  Q  P  Y
R

7081
GCCGGGAGCTGTTCGCCGGTTCCGACGTCACCGACTTCTGCCTCGCCGAACTGCGCGAGA  7140
```

```
         R  E  L  F  A  G  S  D  V  T  D  F  C  L  A  E  L  R  E
T                                                                                     Sau
7141  CCATCGACCGGATCGGCCCGGAGCGGATCGCGGCGATGATCGGCGAGCCGATC
         I  D  R  I  G  P  E  R  I  A  A  M  I  G  E  P  I
```

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 7193 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:1:

```
CCATGGCGGG CGGCGGCTGC CCCGGAGCCT CGGCCGGACC GGTGACCAGG ACCACCCCGG    60
TGGGATAGTG GCCCGCCACC CGGCGCAGCA GACTCCCGGA CACGGACCCG TGGGTGTGCG   120
CGGAAAGGCC CGGAGGCCGG GTCACAGCCA CGGGTAACGC GCGGTGTCCT TGCCCGCGTA   180
ATCGGGGTCC AGATAGACGA AGGCCCGGTG GACGAGGAAG TCCCGCACCT CGTAGACCGT   240
GCACCAGCGC CCGGCGGCCC ACTCGGGGTC ACCCGCCCGC CACGGCCCGT CCCGGTGCTC   300
ACCGTGGGTG GTGCCCTCCG CGGCGAGGAG TTCGGTCCCG GTCAGAATCC AGTTGACGGA   360
CCACAGATGG TGGGTGATCG AGCGGATGGT GCCCCCGAGG TCGTCGAAGA GCCGGGCGAT   420
CTCGGACTTG CCCCGGGCCA GACCCCACTT GGGGAAGAAG AAGACCGCGT CCTCGGCGAA   480
GTAGTCGATC GCGGGGGTGC CGTCGCTGCC GACGCCGCCG TTGTCGAACG CCTTGAAGTA   540
CGCGGTGATG ACCGCCTTGC GCTGCTCGTC CGTCATACCG GCCGATGCCA CGGACATGAA   600
ACGACCTCCA GAGATTCCGG GTGGCTGTGC TGGGGCTGCG GAAGGGGTGT CCCCCGCGAA   660
GGACGGCGGA CGCCGCGGAC GCCGCGGCCG TCTCCCCGGC GGACGGGTCC CAGCGTCCTG   720
GAGAGGGCTT GGCGGCGGCT TGACGCCGTG CTGTCCCGCG GCTTGCGGAA CGCGAAGTAC   780
CGGCCAGCGT ACGGGCGTTG CACCGGACGT GTACGCCGGT CGGGACCCCT CGTACCCCCG   840
GAGCCGGCCG ACCCCGGCGG CTCCGGGGGT ACGGACGCGC CGGACCGGCC CGAGCGAGCC   900
GGACGGGTCG GACGGTGCGC GTGGTTCCGG TGTGTCGGAC AGCTCGGACG GACCGGACGG   960
TGCGCGTGGT TCCGGTGTGT CGGACAGCTC GGACGGGTCG GACGGTGCGC GTGGTTCCGG  1020
CACGCCGGAC GGGTCAGTTG CCGATCATGG CGAGCAATGC CGGGGTGTAC CGCTCCCCGG  1080
ACACCGGGTG GGAGATCGCG GCCGTCACCT CCGCGAGGGA CCGGTCGTCC AGCCGGATCG  1140
AGGCGGCGGC GAGATTGTCC GCGAGATGGG CCGGGTTCGC GGTGCCCGGG ATCGGGACGA  1200
CGTCCTCGCC CCGGTGGTGC AGCCAGGCGA GCGCGAGCTG TGCCAGGGTC AGCCCCAGAC  1260
CGTCCGCGAC CGGGCGCAGC CGGTGCAGCA ACGAGCGGTT GCGCGCGAGG GCCGGAGCGC  1320
TGAACCGGGG CTGGCCCCGG CGGAAGTCCT CGTCCCCCAG ATCGTCGGTG GTGCGGATGG  1380
TGCCGGTGAG AAAACCCCGT CCCAGAGGGG CGTAAGCGAC GATCCCGATC CCCAGCTCCC  1440
GGCAGACGGG CACCACCTCG TCCTCGATCC CGCGCGACCA CAGGCTCCAC TCGCTCTGCA  1500
CCGCCGTCAC CGGGTGCACC GCGTCCGCCC GGCGCAGCGT GGCCGCGGAG GGCTCGGAGA  1560
GACCGAGCCT GCGGACCTTG CCCTCGCGCA CCAGCTCGGC CACCGCACCC ACGGTCTCCT  1620
CGATCGGCAC CGCCGGGTCC GTCCAGTGCT GGTAGTACAG GTCGATGCGG TCGGTGCCGA  1680
GACGACGCAG GGACCGTTCG CAGGCCGCGC GGACGTAGGA CGGCTCGCCG CACAAGCCCT  1740
GGGAGGCGCC GTCGGACGAG CGCACCATGC CGAACTTGGT GGCGATCAGC ACCTCGTCCC  1800
```

-continued

```
GGCGGCCCGC GACCGCCCGT CCGAGCAGCT CCTCACCGGC GCCGAGCCCC TGGACGTCGG   1860
CGGTGTCCAG CAGGGTGACC CCGGCGTCGA CGGCGGCGCG GATGGTGGCC GTCGCCCGGG   1920
CGCGGTCCGG GCGTCCGTAG AAGTCGGTGG TCGGCAGGCA GCCGAGCCCC TGGGCACTGA   1980
CCGGAAGGTC CCGCAGGGCG CGGACCGGCG GACGCGGAAC CGCGGCGGAC ACGGAACCGG   2040
CCGGGGACTC GGGCGGAGAG CGGGACATAC GGAACCTCCA CAGGCGGAGC CGGGAACGGG   2100
ACGAGGGCGA GGACGGGACG GAACGAAGGA GAGGACGGGA CGGACAGCAC GGACGGGACG   2160
GACGGAACGG AGTCGGGAAC CGGGGGGGGT GACCGGAACC GGGCCGTCCT TGGCCCTCCC   2220
CCGTCCTCCC CGCCATCCGC CGTTCTCCCC CGTTCCCTCT CCCGTCCTCC AGCCAACACC   2280
GCCGCCCTTT CCAAGCGCTT GACACGGCAC CGACAGCCGC CGCCGGGCGC CCGATGGGGA   2340
CCCGTGCCCG CCGGTGAGCG GCGGTGAGCG CCGGTACGGG ACCCCACGCG CCGCCGCCCG   2400
GGCGCCCGCC AGGGCCCGCG CGGCCACCCC GGCCCGCCCC GGCGGAGCG GCGATCCGGG    2460
CCGCTCGCTG CAAGAGGAAC ATCCACAGCC GCACAAGGAG CGCTCCGCAC AGTGGGCACC   2520
ACGTCCGCCC CGTCCCCCAC ACCGTGGCCG GTCCCCACCG GACAGCACAG CACCGCACAG   2580
CACCACATCG CACGGCACAG CACAGCACCA CCGGCACGAG GAACCAAGGA AAGGAACCAC   2640
ACCACCATGA CCTCAGTGGA CTGCACCGCG TACGGCCCCG AGCTGCGCGC GCTCGCCGCC   2700
CGGCTGCCCC GGACCCCCCG GGCCGACCTG TACGCCTTCC TGGACGCCGC GCACACAGCC   2760
GCCGCCTCGC TCCCCGGCGC CCTCGCCACC GCGCTGGACA CCTTCAACGC CGAGGGCAGC   2820
GAGGACGGCC ATCTGCTGCT GCGCGGCCTC CCGGTGGAGG CCGACGCCGA CCTCCCCACC   2880
ACCCCGAGCA GCACCCCGGC GCCCGAGGAC CGCTCCCTGC TGACCATGGA GGCCATGCTC   2940
GGACTGGTGG GCCGCCGGCT CGGTCTGCAC ACGGGGTACC GGGAGCTGCG CTCGGGCACG   3000
GTCTACCACG ACGTGTACCC GTCGCCCGGC GCGCACCACC TGTCCTCGGA GACCTCCGAG   3060
ACGCTGCTGG AGTTCCACAC GGAGATGGCC TACCACCGGC TCCAGCCGAA CTACGTCATG   3120
CTGGCCTGCT CCCGGGCCGA CCACGAGCGC ACGGCGGCCA CACTCGTCGC CTCGGTCCGC   3180
AAGGCGCTGC CCCTGCTGGA CGAGAGGACC CGGGCCCGGC TCCTCGACCG GAGGATGCCC   3240
TGCTGCGTGG ATGTGGCCTT CCGCGGCGGG GTGGACGACC CGGGCGCCAT CGCCCAGGTC   3300
AAACCGCTCT ACGGGACGCC GGACGATCCC TTCCTCGGGT ACGACCGCGA GCTGCTGGCG   3360
CCGGAGGACC CCGCGGACAA GGAGGCCGTC GCCGCCCTGT CCAAGGCGCT CGACGAGGTC   3420
ACGGAGGCGG TGTATCTGGA GCCCGGCGAT CTGCTGATCG TCGACAACTT CCGCACCACG   3480
CACGCGCGGA CGCCGTTCTC GCCCCGCTGG ACGGGAAGG ACCGCTGGCT GCACCGCGTC    3540
TACATCCGCA CCGACCGCAA TGGACAGCTC TCCGGCGGCG AGCGCGCGGG CGACGTCGTC   3600
GCCTTCACAC CGCGCGGCTG AGCTCCCGGG TCCGACACCG CGCGGCTGAA CCCACGGTCC   3660
GGGGCCCACG GTCCGGCACC GCGCGGCTGA GCCCCGGGT CCGGCAGCGG GCGGCTGAAC    3720
CCCCGCCCCG GGCCACCGCC CGACCGCCCC CGCGCACCGG ACGCGCCCGC CTGTACGGCG   3780
GTCCCGCCCG GGCCCGTACA CCTGAAGCGC CCGGCGGACC GCCGCCCCGC CGGGGACGG    3840
ACAGAGCCGG GTGCGGAGG ACGTCCTCCC GCACCCGGCT CCCACCGTTC CGCACCGACC    3900
GCACCCGACC GTGCCGCAGG CGCCACCGGC ACCGCACCGC CCGCGCCGGC AGCCACCACA   3960
GGCGCCACGC CGCCCGCACG GTGCCCGCGC TGCTCAGCCC CCGTCCACCG GGCTGTCCAG   4020
CAGCCGCCGC AGCGCGCCCC CGATGAACTC CCGGTCGGCG GCCGACCCCC GGACCCCGC    4080
GAGATGCCCC CACACTCCCG GGATCACCTC CAGCGAGGCA TACGGCAGCA GATCGGCCAC   4140
```

```
CCGCTTCTCG TCCTCGACGG CGAAACACAC GTCCAGGGCG CCCCGGCAGCA CCACGGCCCG    4200

CGCCGTGACG GAGGCCAGCG CCGCCTCGAC GCTCCCCCCG GCCCCGGGTG TCGCCCCCAC    4260

ATCCGTGTTC TCCCAGGTGC GCACCATGGT GAGCAGATCC GCGGCGCCGG GCCCGGAGAG    4320

GAAGACCTGC TCCCAGAAGC CGGTGAGGTA CTCCTCGCGG GTGGCGAAAC CCAGCTCCCG    4380

GTGGGCACGG CGGGCCCAGA AGGAACGCGA GGTCCCCCAC CCGGCGAACA CCCGGCCCGC    4440

CGCCTTCCGC CCCCGCTCCC CGGCGTCGGC GCTGAGCGCC GCGGCCAGAC CGGACAGCAG    4500

GACCAGGCTG TGCGGGCTGC TCACCGGCGC CCCGCAGATC GGGGCGATCC GGCGCACCAT    4560

CCCCGGATGC GACACGGCCC ACTGGTAGGC GTGGGCCGCG CCCATCGACC AGCCCGTGAC    4620

CAGGGCCAGT TCCCGTACCC CCAGCTCCTC GGTGAGCAGC CGGTGCTGCG CCGCGACATT    4680

GTCCTGCGGA GTGATCAGCG GAAAGCGGGA CCCCGACGGG TGGTTGCCGG GCGAGCTGGA    4740

GACCCCGTTG CCGAAGAGTC CGGCGGTGAC GACGCAGTAC CGCCGGGTGT CCAGCGGCAG    4800

CCCCGCACCG ATCAGCCAGT CGTACCCGGT GTGGTCCCGG CCGAAGAACG ACGGACAGAG    4860

CACCACGTTC GTCCCGTCGG CGTTCGGCGT GCCGTACATG GCGTAACCGA TCCGGGCGTC    4920

CCGCAGGACC TCCCCGTCCA GCAACGGCAG TTCGTCGATC TCGAATATGC GGCATTCCAC    4980

CGCTGACCTC CTTGTTCGAT CCCCCCGGAC AACAGGTCGG TCGTGGCCGG AGACTCAGAG    5040

CCAGTTGGGG GCGATCTCGG TGGCCCACAG CTCCAGGCTG CGCAGCTGGA CATCGTGCGG    5100

GATCAGCCCG GAGTACTGGC ACTGGAGCAG ATACTCCGGA TCGTGCCGCT CCACCAGCTT    5160

CTCGATCATG CGGTTGATGT CGTCCGGGGT GCCGACCCAC TCCAGCCCCC GGTCGACCAG    5220

GGTCTTGTAG TCCGAGCCGA TCGGACCCGT CTCGCCGGTC GCGCGCAGCG CCTCGGTGAA    5280

GCCCATGGGG CCGAACCAGT TCTCGAAGAT GAAGCCGCCG CCGCGGGACG CCCAGTGGTG    5340

GGCCTCGCCG GAGTCCCGGG AGACCAGGAC GTCCTTCATC ACCCCGACCC GCTCGCCCCG    5400

CCGCAGGGTG CCGTGGCCCG CCGCCTCGGC CTCCTCCCGG TAGATGTCCA TCAGCCGGGC    5460

GACGATCTGG TCGTCGGTGT TCATCAGGAT CGGCACCACG CCCTCCCGGG CACAGAACCG    5520

GAACGTGTCC TCACTGAAGC TGAACGGCTG GAAGACGGGC GGGTGGGGGC GCTGGTAGGG    5580

CTTGGGCGCG ATGCCCACCT CGCGGATGAC GCCGTTCTCG TCGAGGCCCC GGCCGTAGCG    5640

GCGCACCGCC TCGTAGGGGA ACTCCAGGTC CGGCACCGGG ATCGTCCACT GCTCCCCGGA    5700

GTGGGTGAAC GTCTCGGTCG TCCACGCCTT CTTGATGATC TCCCAGTGCT CCTCGAAGAG    5760

GGCACGATTG CGCCGGTCCC GCTCCCCGGC GTCGGACAGG GTGCCGCCGA CCCCGTACAC    5820

CTGCCCCATG ATGTCGGCCC AGCGCTTCTG GAACCCGCGC GCGATCCCGA CGAAGGCGCG    5880

GCCCCGGGTC ATGTGGTCGA GCATCGCCAG ATCCTCGGCC AGCCGCAGCG GATTGTGCAG    5940

CGGCAGGACG TTGGCCATCT GGCCGACCCG GATGTGCCGG GTCTGCATGC CGAGGTAGAG    6000

CCCCAGCATG ATCGGGTTGT TGGAGACCTC GAAACCCTCG GTGTGGAAGT GGTGCTCGGT    6060

GAAGGACAGT CCCCAGTAGC CGAGTTCGTC GGCCGCCTGC GCCTGCCGGG TGAGCTGCCG    6120

GAGCATGTTC TGGTAGTTCT GCGGATTGAC CCCCGCCATA CCCCGCTGGA CCTGCGCATG    6180

ACTGCCGACC GTTGGCAGAT AGAAGAGAAT GGACTTCACC CTGGCTCCTC CGGTTCGCGG    6240

CGCCCTCCAT TGACGTGCGC CGAAAGCGGC TCGACCGTCC CACTCCGCCC TTGAGTTCCG    6300

TCTGACGCCG CGCCAGTCGG CGGGCCGTCC GCCGGGGTGC CCGCCGGGGT CCGCACCCGC    6360

CGGACGGCAC GGCGCGCACC GCGCGCGCGG CGCTTCGGGG CACCGGGCTC GACGGGGTGC    6420

TCAGCGGGAC GTCAACGGA AGGCAAGCCC CCGTACCCAG CCTGGTCAAG GCGCTCATCG    6480

CCATTCCCTG AGGAGGTCCC GCCTTGACCA CAGCAATCTC CGCGCTCCCG ACCGTGCCCG    6540
```

```
GCTCCGGACT CGAAGCACTG GACCGTGCCA CCCTCATCCA CCCCACCCTC TCCGGAAACA        6600

CCGCGGAACG GATCGTGCTG ACCTCGGGGT CCGGCAGCCG GGTCCGCGAC ACCGACGGCC        6660

GGGAGTACCT GGACGCGAGC GCCGTCCTCG GGGTGACCCA GGTGGGCCAC GGCCGGGCCG        6720

AGCTGGCCCG GGTCGCGGCC GAGCAGATGG CCCGGCTGGA GTACTTCCAC ACCTGGGGGA        6780

CGATCAGCAA CGACCGGGCG GTGGAGCTGG CGGCACGGCT GGTGGGGCTG AGCCCGGAGC        6840

CGCTGACCCG CGTCTACTTC ACCAGCGGCG GGGCCGAGGG CAACGAGATC GCCCTGCGGA        6900

TGGCCCGGCT CTACCACCAC CGGCGCGGGG AGTCCGCCCG TACCTGGATA CTCTCCCGCC        6960

GGTCGGCCTA CCACGGCGTC GGATACGGCA GCGGCGGCGT CACCGGCTTC CCCGCCTACC        7020

ACCAGGGCTT CGGCCCCTCC CTCCCGGACG TCGACTTCCT GACCCCGCCG CAGCCCTACC        7080

GCCGGGAGCT GTTCGCCGGT TCCGACGTCA CCGACTTCTG CCTCGCCGAA CTGCGCGAGA        7140

CCATCGACCG GATCGGCCCG GAGCGGATCG CGGCGATGAT CGGCGAGCCG ATC             7193

(2) INFORMATION FOR SEQ ID NO:2:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:2:

GTGACCCGGC CTCCGGGCCT TTCCGCGCAC ACCCACGGGT CCGTGTCCGG GAGTCTGCTG         60

CGCCGGGTGG CGGGCCACTA TCCCACCGGG GTGGTCCTGG TCACCGGTCC GGCCGAGGCT        120

CCGGGGCAGC CGCCGCCCGC CATGG                                             145

(2) INFORMATION FOR SEQ ID NO:3:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

ATGTCCGTGG CATCGGCCGG TATGACGGAC GAGCAGCGCA AGGCGGTCAT CACCGCGTAC         60

TTCAAGGCGT TCGACAACGG CGGCGTCGGC AGCGACGGCA CCCCCGCGAT CGACTACTTC        120

GCCGAGGACG CGGTCTTCTT CTTCCCCAAG TGGGGTCTGG CCCGGGGCAA GTCCGAGATC        180

GCCCGGCTCT TCGACGACCT CGGGGGCACC ATCCGCTCGA TCACCCACCA TCTGTGGTCC        240

GTCAACTGGA TTCTGACCGG GACCGAACTC CTCGCCGCGG AGGCACCAC CCACGGTGAG         300

CACCGGGACG GGCCGTGGCG GGCGGGTGAC CCCGAGTGGG CCGCCGGGCG CTGGTGCACG        360

GTCTACGAGG TGCGGGACTT CCTCGTCCAC CGGGCCTTCG TCTATCTGGA CCCCGATTAC        420

GCGGGCAAGG ACACCGCGCG TTACCCGTGG CTG                                    453

(2) INFORMATION FOR SEQ ID NO:4:

(i) SEQUENCE CHARACTERISTICS:
        (A) LENGTH: 1032 base pairs
        (B) TYPE: nucleic acid
        (C) STRANDEDNESS: single
        (D) TOPOLOGY: linear
```

(ii) MOLECULE TYPE: Other (xi) SEQUENCE DESCRIPTION: SEQ ID NO:4:

| | | | | | |
|---|---|---|---|---|---|
| ATGTCCCGCT | CTCCGCCCGA | GTCCCCGGCC | GGTTCCGTGT | CCGCCGCGGT | TCCGCGTCCG | 60 |
| CCGGTCCGCG | CCCTGCGGGA | CCTTCCGGTC | AGTGCCCAGG | GGCTCGGCTG | CCTGCCGACC | 120 |
| ACCGACTTCT | ACGGACGCCC | GGACCGCGCC | CGGGCGACGG | CCACCATCCG | CGCCGCCGTC | 180 |
| GACGCCGGGG | TCACCCTGCT | GGACACCGCC | GACGTCCAGG | GGCTCGGCGC | CGGTGAGGAG | 240 |
| CTGCTCGGAC | GGGCGGTCGC | GGGCCGCCGG | GACGAGGTGC | TGATCGCCAC | CAAGTTCGGC | 300 |
| ATGGTGCGCT | CGTCCGACGG | CGCCTCCCAG | GGCTTGTGCG | GCGAGCCGTC | CTACGTCCGC | 360 |
| GCGGCCTGCG | AACGGTCCCT | GCGTCGTCTC | GGCACCGACC | GCATCGACCT | GTACTACCAG | 420 |
| CACTGGACGG | ACCCGGCGGT | GCCGATCGAG | GAGACCGTGG | GTGCGGTGGC | CGAGCTGGTG | 480 |
| CGCGAGGGCA | AGGTCCGCAG | GCTCGGTCTC | TCCGAGCCCT | CCGCGGCCAC | GCTGCGCCGG | 540 |
| GCGGACGCGG | TGCACCCGGT | GACGGCGGTG | CAGAGCGAGT | GGAGCCTGTG | GTCGCGCGGG | 600 |
| ATCGAGGACG | AGGTGGTGCC | CGTCTGCCGG | GAGCTGGGGA | TCGGGATCGT | CGCTTACGCC | 660 |
| CCTCTGGGAC | GGGGTTTTCT | CACCGGCACC | ATCCGCACCA | CCGACGATCT | GGGGGACGAG | 720 |
| GACTTCCGCC | GGGGCCAGCC | CCGGTTCAGC | GCTCCGGCCC | TCGCGCGCAA | CCGCTCGTTG | 780 |
| CTGCACCGGC | TGCGCCCGGT | CGCGGACGGT | CTGGGGCTGA | CCCTGGCACA | GCTCGCGCTC | 840 |
| GCCTGGCTGC | ACCACCGGGG | CGAGGACGTC | GTCCCGATCC | CGGGCACCGC | GAACCCGGCC | 900 |
| CATCTCGCGG | ACAATCTCGC | CGCCGCCTCG | ATCCGGCTGG | ACGACCGGTC | CCTCGCGGAG | 960 |
| GTGACGGCCG | CGATCTCCCA | CCCGGTGTCC | GGGGAGCGGT | ACACCCCGGC | ATTGCTCGCC | 1020 |
| ATGATCGGCA | AC | | | | | 1032 |

(2) INFORMATION FOR SEQ ID NO:5:

(i) SEQUENCE CHARACTERISTICS:
        (A) LENGTH: 984 base pairs (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

| | | | | | |
|---|---|---|---|---|---|
| GTGGAATGCC | GCATATTCGA | GATCGACGAA | CTGCCGTTGC | TGGACGGGGA | GGTCCTGCGG | 60 |
| GACGCCCGGA | TCGGTTACGC | CATGTACGGC | ACGCCGAACG | CCGACGGGAC | GAACGTGGTG | 120 |
| CTCTGTCCGT | CGTTCTTCGG | CCGGGACCAC | ACCGGGTACG | ACTGGCTGAT | CGGTGCGGGG | 180 |
| CTGCCGCTGG | ACACCCGGCG | GTACTGCGTC | GTCACCGCCG | GACTCTTCGG | CAACGGGGTC | 240 |
| TCCAGCTCGC | CCGGCAACCA | CCCGTCGGGG | TCCCGCTTTC | CGCTGATCAC | TCCGCAGGAC | 300 |
| AATGTCGCGG | CGCAGCACCG | GCTGCTCACC | GAGGAGCTGG | GGTACGGGA | ACTGGCCCTG | 360 |
| GTCACGGGCT | GGTCGATGGG | CGCGGCCCAC | GCCTACCAGT | GGGCCGTGTC | GCATCCGGGG | 420 |
| ATGGTGCGCC | GGATCGCCCC | GATCTGCGGG | GCGCCGGTGA | GCAGCCCGCA | CAGCCTGGTC | 480 |
| CTGCTGTCCG | GTCTGGCCGC | GGCGCTCAGC | GCCGACGCCG | GGGAGCGGGG | GCGGAAGGCG | 540 |
| GCGGGCCGGG | TGTTCGCCGG | GTGGGGGACC | TCGCGTTCCT | TCTGGGCCCG | CCGTGCCCAC | 600 |
| CGGGAGCTGG | GTTTCGCCAC | CCGCGAGGAG | TACCTCACCG | GCTTCTGGGA | GCAGGTCTTC | 660 |
| CTCTCCGGGC | CCGGCGCCGC | GGATCTGCTC | ACCATGGTGC | GCACCTGGGA | GAACACGGAT | 720 |

```
                                                  -continued
GTGGGGGCGA CACCCGGGGC CGGGGGGAGC GTCGAGGCGG CGCTGGCCTC CGTCACGGCG      780

CGGGCCGTGG TGCTGCCGGG CGCCCTGGAC GTGTGTTTCG CCGTCGAGGA CGAGAAGCGG      840

GTGGCCGATC TGCTGCCGTA TGCCTCGCTG GAGGTGATCC CGGGAGTGTG GGGGCATCTC      900

GCGGGGTCCG GGGGGTCGGC CGCCGACCGG GAGTTCATCG GGGGCGCGCT GCGGCGGCTG      960

CTGGACAGCC CGGTGGACGG GGGC                                            984
```

(2) INFORMATION FOR SEQ ID NO:6:

(i) SEQUENCE CHARACTERISTICS:
    (A) LENGTH: 1182 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:6:

```
GTGAAGTCCA TTCTCTTCTA TCTGCCAACG GTCGGCAGTC ATGCGCAGGT CCAGCGGGGT       60

ATGGCGGGGG TCAATCCGCA GAACTACCAG AACATGCTCC GGCAGCTCAC CCGGCAGGCG      120

CAGGCGGCCG ACGAACTCGG CTACTGGGGA CTGTCCTTCA CCGAGCACCA CTTCCACACC      180

GAGGGTTTCG AGGTCTCCAA CAACCCGATC ATGCTGGGGC TCTACCTCGG CATGCAGACC      240

CGGCACATCC GGGTCGGCCA GATGGCCAAC GTCCTGCCGC TGCACAATCC GCTGCGGCTG      300

GCCGAGGATC TGGCGATGCT CGACCACATG ACCCGGGGCC GCGCCTTCGT CGGGATCGCG      360

CGCGGGTTCC AGAAGCGCTG GGCCGACATC ATGGGGCAGG TGTACGGGGT CGGCGGCACC      420

CTGTCCGACG CCGGGGAGCG GGACCGGCGC AATCGTGCCC TCTTCGAGGA GCACTGGGAG      480

ATCATCAAGA AGGCGTGGAC GACCGAGACG TTCACCCACT CCGGGGAGCA GTGGACGATC      540

CCGGTGCCGG ACCTGGAGTT CCCCTACGAG GCGGTGCGCC GCTACGGCCG GGGCCTCGAC      600

GAGAACGGCG TCATCCGCGA GGTGGGCATC GCGCCCAAGC CCTACCAGCG CCCCCACCCG      660

CCCGTCTTCC AGCCGTTCAG CTTCAGTGAG GACACGTTCC GGTTCTGTGC CCGGGAGGGC      720

GTGGTGCCGA TCCTGATGAA CACCGACGAC CAGATCGTCG CCCGGCTGAT GGACATCTAC      780

CGGGAGGAGG CCGAGGCGGC GGGCCACGGC ACCCTGCGGC GGGGCGAGCG GGTCGGGGTG      840

ATGAAGGACG TCCTGGTCTC CCGGGACTCC GGCGAGGCCC ACCACTGGGC GTCCCGCGGC      900

GGCGGCTTCA TCTTCGAGAA CTGGTTCGGC CCCATGGGCT TCACCGAGGC GCTGCGCGCG      960

ACCGGCGAGA CGGGTCCGAT CGGCTCGGAC TACAAGACCC TGGTCGACCG GGGGCTGGAG     1020

TGGGTCGGCA CCCCGGACGA CATCAACCGC ATGATCGAGA AGCTGGTGGA GCGGCACGAT     1080

CCGGAGTATC TGCTCCAGTG CCAGTACTCC GGGCTGATCC CGCACGATGT CCAGCTGCGC     1140

AGCCTGGAGC TGTGGGCCAC CGAGATCGCC CCCAACTGGC TC                       1182
```

(2) INFORMATION FOR SEQ ID NO:7:

(i) SEQUENCE CHARACTERISTICS:
    (A) LENGTH: 660 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:7:

```
GTGCCCGGCT CCGGACTCGA AGCACTGGAC CGTGCCACCC TCATCCACCC CACCCTCTCC       60

GGAAACACCG CGGAACGGAT CGTGCTGACC TCGGGGTCCG GCAGCCGGGT CCGCGACACC      120
```

```
GACGGCCGGG AGTACCTGGA CGCGAGCGCC GTCCTCGGGG TGACCCAGGT GGGCCACGGC    180

CGGGCCGAGC TGGCCCGGGT CGCGGCCGAG CAGATGGCCC GGCTGGAGTA CTTCCACACC    240

TGGGGGACGA TCAGCAACGA CCGGGCGGTG GAGCTGGCGG CACGGCTGGT GGGGCTGAGC    300

CCGGAGCCGC TGACCCGCGT CTACTTCACC AGCGGCGGGG CCGAGGGCAA CGAGATCGCC    360

CTGCGGATGG CCCGGCTCTA CCACCACCGG CGCGGGGAGT CCGCCCGTAC CTGGATACTC    420

TCCCGCCGGT CGGCCTACCA CGGCGTCGGA TACGGCAGCG GCGGCGTCAC CGGCTTCCCC    480

GCCTACCACC AGGGCTTCGG CCCCTCCCTC CCGGACGTCG ACTTCCTGAC CCCGCCGCAG    540

CCCTACCGCC GGGAGCTGTT CGCCGGTTCC GACGTCACCG ACTTCTGCCT CGCCGAACTG    600

CGCGAGACCA TCGACCGGAT CGGCCCGGAG CGGATCGCGG CGATGATCGG CGAGCCGATC    660
```

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

```
CTGACGCTGC AGGAGGAAGT CCCGC                                           25
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

```
CGGGGCGAGG ACGTCGTCCC GATCC                                           25
```

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

```
GAGCCCCTGG ACGTCGGCGG TGTCC                                           25
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

```
GACGGTGCAT GCTCAGCAGG GAGCG                                           25
```

(2) INFORMATION FOR SEQ ID NO:12:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

```
ATGACCTCAG TGGACTGCAC CGCGTACGGC CCCGAGCTGC GCGCGCTCGC CGCCCGGCTG      60
CCCCGGACCC CCCGGGCCGA CCTGTACGCC TTCCTGGACG CCGCGCACAC AGCCGCCGCC     120
TCGCTCCCCG GCGCCCTCGC CACCGCGCTG GACACCTTCA ACGCCGAGGG CAGCGAGGAC     180
GGCCATCTGC TGCTGCGCGG CCTCCCGGTG GAGGCCGACG CCGACCTCCC CACCACCCCG     240
AGCAGCACCC CGGCGCCCGA GGACCGCTCC CTGCTGACCA TGGAGGCCAT GCTCGGACTG     300
GTGGGCCGCC GGCTCGGTCT GCACACGGGG TACCGGGAGC TGCGCTCGGG CACGGTCTAC     360
CACGACGTGT ACCCGTCGCC CGGCGCGCAC CACCTGTCCT CGGAGACCTC CGAGACGCTG     420
CTGGAGTTCC ACACGGAGAT GGCCTACCAC CGGCTCCAGC CGAACTACGT CATGCTGGCC     480
TGCTCCCGGG CCGACCACGA CGCACGGCG GCCACACTCG TCGCCTCGGT CCGCAAGGCG     540
CTGCCCCTGC TGGACGAGAG GACCCGGGCC CGGCTCCTCG ACCGGAGGAT GCCCTGCTGC     600
GTGGATGTGG CCTTCCGCGG CGGGGTGGAC GACCCGGGCG CCATCGCCCA GGTCAAACCG     660
CTCTACGGGG ACGCGGACGA TCCCTTCCTC GGGTACGACC GCGAGCTGCT GGCGCCGGAG     720
GACCCCGCGG ACAAGGAGGC CGTCGCCGCC CTGTCCAAGG CGCTCGACGA GGTCACGGAG     780
GCGGTGTATC TGGAGCCCGG CGATCTGCTG ATCGTCGACA ACTTCCGCAC CACGCACGCG     840
CGGACGCCGT TCTCGCCCCG CTGGGACGGG AAGGACCGCT GGCTGCACCG CGTCTACATC     900
CGCACCGACC GCAATGGACA GCTCTCCGGC GGCGAGCGCG CGGGCGACGT CGTCGCCTTC     960
ACACCGCGCG GC                                                        972
```

(2) INFORMATION FOR SEQ ID NO:13:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Met Thr Arg Pro Pro Gly Leu Ser Ala His Thr His Gly Ser Val Ser
 1               5                  10                  15

Gly Ser Leu Leu Arg Arg Val Ala Gly His Tyr Pro Thr Gly Val Val
                20                  25                  30

Leu Val Thr Gly Pro Ala Glu Ala Pro Gly Gln Pro Pro Ala Met
            35                  40                  45
```

(2) INFORMATION FOR SEQ ID NO:14:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Ser Val Ala Ser Ala Gly Met Thr Asp Glu Gln Arg Lys Ala Val
1               5                   10                  15

Ile Thr Ala Tyr Phe Lys Ala Phe Asp Asn Gly Val Gly Ser Asp
                20                  25                  30

Gly Thr Pro Ala Ile Asp Tyr Phe Ala Glu Asp Ala Val Phe Phe Phe
                35                  40                  45

Pro Lys Trp Gly Leu Ala Arg Gly Lys Ser Glu Ile Ala Arg Leu Phe
                50                  55                  60

Asp Asp Leu Gly Gly Thr Ile Arg Ser Ile Thr His His Leu Trp Ser
65                  70                  75                  80

Val Asn Trp Ile Leu Thr Gly Thr Glu Leu Leu Ala Ala Glu Gly Thr
                85                  90                  95

Thr His Gly Glu His Arg Asp Gly Pro Trp Arg Ala Gly Asp Pro Glu
                100                 105                 110

Trp Ala Ala Gly Arg Trp Cys Thr Val Tyr Glu Val Arg Asp Phe Leu
                115                 120                 125

Val His Arg Ala Phe Val Tyr Leu Asp Pro Asp Tyr Ala Gly Lys Asp
                130                 135                 140

Thr Ala Arg Tyr Pro Trp Leu
145                 150
```

(2) INFORMATION FOR SEQ ID NO:15:

(i) SEQUENCE CHARACTERISTICS:
        (A) LENGTH: 344 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Met Ser Arg Ser Pro Pro Glu Ser Pro Ala Gly Ser Val Ser Ala Ala
1               5                   10                  15

Val Pro Arg Pro Pro Val Arg Ala Leu Arg Asp Leu Pro Val Ser Ala
                20                  25                  30

Gln Gly Leu Gly Cys Leu Pro Thr Thr Asp Phe Tyr Gly Arg Pro Asp
                35                  40                  45

Arg Ala Arg Ala Thr Ala Thr Ile Arg Ala Ala Val Asp Ala Gly Val
                50                  55                  60

Thr Leu Leu Asp Thr Ala Asp Val Gln Gly Leu Gly Ala Gly Glu Glu
65                  70                  75                  80

Leu Leu Gly Arg Ala Val Ala Gly Arg Arg Asp Glu Val Leu Ile Ala
                85                  90                  95

Thr Lys Phe Gly Met Val Arg Ser Ser Asp Gly Ala Ser Gln Gly Leu
                100                 105                 110

Cys Gly Glu Pro Ser Tyr Val Arg Ala Ala Cys Glu Arg Ser Leu Arg
                115                 120                 125

Arg Leu Gly Thr Asp Arg Ile Asp Leu Tyr Tyr Gln His Trp Thr Asp
                130                 135                 140

Pro Ala Val Pro Ile Glu Glu Thr Val Gly Ala Val Ala Glu Leu Val
145                 150                 155                 160

Arg Glu Gly Lys Val Arg Arg Leu Gly Leu Ser Glu Pro Ser Ala Ala
                165                 170                 175
```

```
Thr Leu Arg Arg Ala Asp Ala Val His Pro Val Thr Ala Val Gln Ser
            180                 185                 190

Glu Trp Ser Leu Trp Ser Arg Gly Ile Glu Asp Glu Val Val Pro Val
            195                 200                 205

Cys Arg Glu Leu Gly Ile Gly Ile Val Ala Tyr Ala Pro Leu Gly Arg
            210                 215                 220

Gly Phe Leu Thr Gly Thr Ile Arg Thr Thr Asp Asp Leu Gly Asp Glu
225                 230                 235                 240

Asp Phe Arg Arg Gly Gln Pro Arg Phe Ser Ala Pro Ala Leu Ala Arg
            245                 250                 255

Asn Arg Ser Leu Leu His Arg Leu Arg Pro Val Ala Asp Gly Leu Gly
            260                 265                 270

Leu Thr Leu Ala Gln Leu Ala Leu Ala Trp Leu His His Arg Gly Glu
            275                 280                 285

Asp Val Val Pro Ile Pro Gly Thr Ala Asn Pro Ala His Leu Ala Asp
            290                 295                 300

Asn Leu Ala Ala Ala Ser Ile Arg Leu Asp Asp Arg Ser Leu Ala Glu
305                 310                 315                 320

Val Thr Ala Ala Ile Ser His Pro Val Ser Gly Glu Arg Tyr Thr Pro
                    325                 330                 335

Ala Leu Leu Ala Met Ile Gly Asn
            340

(2) INFORMATION FOR SEQ ID NO:16:

(i) SEQUENCE CHARACTERISTICS:
        (A) LENGTH: 328 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Met Glu Cys Arg Ile Phe Glu Ile Asp Glu Leu Pro Leu Leu Asp Gly
1               5                   10                  15

Glu Val Leu Arg Asp Ala Arg Ile Gly Tyr Ala Met Tyr Gly Thr Pro
            20                  25                  30

Asn Ala Asp Gly Thr Asn Val Val Leu Cys Pro Ser Phe Phe Gly Arg
            35                  40                  45

Asp His Thr Gly Tyr Asp Trp Leu Ile Gly Ala Gly Leu Pro Leu Asp
            50                  55                  60

Thr Arg Arg Tyr Cys Val Val Thr Ala Gly Leu Phe Gly Asn Gly Val
65                  70                  75                  80

Ser Ser Ser Pro Gly Asn His Pro Ser Gly Ser Arg Phe Pro Leu Ile
            85                  90                  95

Thr Pro Gln Asp Asn Val Ala Ala Gln His Arg Leu Leu Thr Glu Glu
            100                 105                 110

Leu Gly Val Arg Glu Leu Ala Leu Val Thr Gly Trp Ser Met Gly Ala
            115                 120                 125

Ala His Ala Tyr Gln Trp Ala Val Ser His Pro Gly Met Val Arg Arg
            130                 135                 140

Ile Ala Pro Ile Cys Gly Ala Pro Val Ser Ser Pro His Ser Leu Val
145                 150                 155                 160

Leu Leu Ser Gly Leu Ala Ala Leu Ser Ala Asp Ala Gly Glu Arg
            165                 170                 175
```

-continued

Gly Arg Lys Ala Ala Gly Arg Val Phe Ala Gly Trp Gly Thr Ser Arg
              180                 185                 190

Ser Phe Trp Ala Arg Arg Ala His Arg Glu Leu Gly Phe Ala Thr Arg
        195                 200                 205

Glu Glu Tyr Leu Thr Gly Phe Trp Glu Gln Val Phe Leu Ser Gly Pro
    210                 215                 220

Gly Ala Ala Asp Leu Leu Thr Met Val Arg Thr Trp Glu Asn Thr Asp
225                 230                 235                 240

Val Gly Ala Thr Pro Gly Ala Gly Ser Val Glu Ala Ala Leu Ala
                245                 250                 255

Ser Val Thr Ala Arg Ala Val Val Leu Pro Gly Ala Leu Asp Val Cys
                260                 265                 270

Phe Ala Val Glu Asp Glu Lys Arg Val Ala Asp Leu Leu Pro Tyr Ala
            275                 280                 285

Ser Leu Glu Val Ile Pro Gly Val Trp Gly His Leu Ala Gly Ser Gly
        290                 295                 300

Gly Ser Ala Ala Asp Arg Glu Phe Ile Gly Gly Ala Leu Arg Arg Leu
305                 310                 315                 320

Leu Asp Ser Pro Val Asp Gly Gly
                325

(2) INFORMATION FOR SEQ ID NO:17:

(i) SEQUENCE CHARACTERISTICS:
        (A) LENGTH: 394 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Met Lys Ser Ile Leu Phe Tyr Leu Pro Thr Val Gly Ser His Ala Gln
  1                 5                  10                  15

Val Gln Arg Gly Met Ala Gly Val Asn Pro Gln Asn Tyr Gln Asn Met
                20                  25                  30

Leu Arg Gln Leu Thr Arg Gln Ala Gln Ala Ala Asp Glu Leu Gly Tyr
            35                  40                  45

Trp Gly Leu Ser Phe Thr Glu His His Phe His Thr Glu Gly Phe Glu
    50                  55                  60

Val Ser Asn Asn Pro Ile Met Leu Gly Leu Tyr Leu Gly Met Gln Thr
 65                 70                  75                  80

Arg His Ile Arg Val Gly Gln Met Ala Asn Val Leu Pro Leu His Asn
                85                  90                  95

Pro Leu Arg Leu Ala Glu Asp Leu Ala Met Leu Asp His Met Thr Arg
            100                 105                 110

Gly Arg Ala Phe Val Gly Ile Ala Arg Gly Phe Gln Lys Arg Trp Ala
        115                 120                 125

Asp Ile Met Gly Gln Val Tyr Gly Val Gly Thr Leu Ser Asp Ala
        130                 135                 140

Gly Glu Arg Asp Arg Arg Asn Arg Ala Leu Phe Glu Glu His Trp Glu
145                 150                 155                 160

Ile Ile Lys Lys Ala Trp Thr Thr Glu Thr Phe Thr His Ser Gly Glu
                165                 170                 175

Gln Trp Thr Ile Pro Val Pro Asp Leu Glu Phe Pro Tyr Glu Ala Val
            180                 185                 190

```
Arg Arg Tyr Gly Arg Gly Leu Asp Glu Asn Gly Val Ile Arg Glu Val
        195                 200                 205

Gly Ile Ala Pro Lys Pro Tyr Gln Arg Pro His Pro Pro Val Phe Gln
        210                 215                 220

Pro Phe Ser Phe Ser Glu Asp Thr Phe Arg Phe Cys Ala Arg Glu Gly
225                 230                 235                 240

Val Val Pro Ile Leu Met Asn Thr Asp Asp Gln Ile Val Ala Arg Leu
                245                 250                 255

Met Asp Ile Tyr Arg Glu Glu Ala Glu Ala Gly His Gly Thr Leu
                260                 265                 270

Arg Arg Gly Glu Arg Val Gly Val Met Lys Asp Val Leu Val Ser Arg
        275                 280                 285

Asp Ser Gly Glu Ala His His Trp Ala Ser Arg Gly Gly Phe Ile
        290                 295                 300

Phe Glu Asn Trp Phe Gly Pro Met Gly Phe Thr Glu Ala Leu Arg Ala
305                 310                 315                 320

Thr Gly Glu Thr Gly Pro Ile Gly Ser Asp Tyr Lys Thr Leu Val Asp
                325                 330                 335

Arg Gly Leu Glu Trp Val Gly Thr Pro Asp Asp Ile Asn Arg Met Ile
                340                 345                 350

Glu Lys Leu Val Glu Arg His Asp Pro Glu Tyr Leu Leu Gln Cys Gln
        355                 360                 365

Tyr Ser Gly Leu Ile Pro His Asp Val Gln Leu Arg Ser Leu Glu Leu
        370                 375                 380

Trp Ala Thr Glu Ile Ala Pro Asn Trp Leu
385                 390

(2) INFORMATION FOR SEQ ID NO:18:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Met Pro Gly Ser Gly Leu Glu Ala Leu Asp Arg Ala Thr Leu Ile His
1               5                   10                  15

Pro Thr Leu Ser Gly Asn Thr Ala Glu Arg Ile Val Leu Thr Ser Gly
                20                  25                  30

Ser Gly Ser Arg Val Arg Asp Thr Asp Gly Arg Glu Tyr Leu Asp Ala
        35                  40                  45

Ser Ala Val Leu Gly Val Thr Gln Val Gly His Gly Arg Ala Glu Leu
        50                  55                  60

Ala Arg Val Ala Ala Glu Gln Met Ala Arg Leu Glu Tyr Phe His Thr
65                  70                  75                  80

Trp Gly Thr Ile Ser Asn Asp Arg Ala Val Glu Leu Ala Ala Arg Leu
                85                  90                  95

Val Gly Leu Ser Pro Glu Pro Leu Thr Arg Val Tyr Phe Thr Ser Gly
                100                 105                 110

Gly Ala Glu Gly Asn Glu Ile Ala Leu Arg Met Ala Arg Leu Tyr His
        115                 120                 125

His Arg Arg Gly Glu Ser Ala Arg Thr Trp Ile Leu Ser Arg Arg Ser
        130                 135                 140
```

```
Ala Tyr His Gly Val Gly Tyr Gly Ser Gly Gly Val Thr Gly Phe Pro
145                 150                 155                 160

Ala Tyr His Gln Gly Phe Gly Pro Ser Leu Pro Asp Val Asp Phe Leu
            165                 170                 175

Thr Pro Pro Gln Pro Tyr Arg Arg Glu Leu Phe Ala Gly Ser Asp Val
            180                 185                 190

Thr Asp Phe Cys Leu Ala Glu Leu Arg Glu Thr Ile Asp Arg Ile Gly
        195                 200                 205

Pro Glu Arg Ile Ala Ala Met Ile Gly Glu Pro Ile
210                 215                 220
```

(2) INFORMATION FOR SEQ ID NO:19:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: protei (xi) SEQUENCE DESCRIPTION: SEQ ID NO:19:

```
Met Thr Ser Val Asp Cys Thr Ala Tyr Gly Pro Glu Leu Arg Ala Leu
1               5                   10                  15

Ala Ala Arg Leu Pro Arg Thr Pro Arg Ala Asp Leu Tyr Ala Phe Leu
            20                  25                  30

Asp Ala His Thr Ala Ala Ala Ser Leu Pro Gly Ala Leu Ala Thr
        35                  40                  45

Ala Leu Asp Thr Phe Asn Ala Glu Gly Ser Glu Asp Gly His Leu Leu
50                  55                  60

Leu Arg Gly Leu Pro Val Glu Ala Asp Ala Asp Leu Pro Thr Thr Pro
65                  70                  75                  80

Ser Ser Thr Pro Ala Pro Glu Asp Arg Ser Leu Leu Thr Met Glu Ala
            85                  90                  95

Met Leu Gly Leu Val Gly Arg Arg Leu Gly Leu His Thr Gly Tyr Arg
            100                 105                 110

Glu Leu Arg Ser Gly Thr Val Tyr His Asp Val Tyr Pro Ser Pro Gly
            115                 120                 125

Ala His His Leu Ser Ser Glu Thr Ser Glu Thr Leu Leu Glu Phe His
130                 135                 140

Thr Glu Met Ala Tyr His Arg Leu Gln Pro Asn Tyr Val Met Leu Ala
145                 150                 155                 160

Cys Ser Arg Ala Asp His Glu Arg Thr Ala Ala Thr Leu Val Ala Ser
                165                 170                 175

Val Arg Lys Ala Leu Pro Leu Leu Asp Glu Arg Thr Arg Ala Arg Leu
            180                 185                 190

Leu Asp Arg Arg Met Pro Cys Cys Val Asp Val Ala Phe Arg Gly Gly
        195                 200                 205

Val Asp Asp Pro Gly Ala Ile Ala Gln Val Lys Pro Leu Tyr Gly Asp
210                 215                 220

Ala Asp Asp Pro Phe Leu Gly Tyr Asp Arg Glu Leu Leu Ala Pro Glu
225                 230                 235                 240

Asp Pro Ala Asp Lys Glu Ala Val Ala Ala Leu Ser Lys Ala Leu Asp
            245                 250                 255

Glu Val Thr Glu Ala Val Tyr Leu Glu Pro Gly Asp Leu Leu Ile Val
            260                 265                 270
```

```
-continued

Asp Asn Phe Arg Thr Thr His Ala Arg Thr Pro Phe Ser Pro Arg Trp
        275                 280                 285

Asp Gly Lys Asp Arg Trp Leu His Arg Val Tyr Ile Arg Thr Asp Arg
    290             295                 300

Asn Gly Gln Leu Ser Gly Gly Glu Arg Ala Gly Asp Val Val Ala Phe
305                 310                 315                 320

Thr Pro Arg Gly
```

US 6,936,458 B1

ISOLATED DNA COMPRISING ONE OR MORE GENES SPECIFIC FOR 5S CLAVAM BIOSYNTHESIS, VECTORS COMPRISING SUCH DNA AND STREPTOMYCES HOSTS CAPABLE OF IMPROVED CLAVULANIC ACID PRODUCTION

CROSS REFERENCE TO RELATED APPLICATIONS

This application is a divisional of application Ser. No. 09/018,806, filed Feb. 4, 1998 now abandoned, which claims priority from GB 9702218.0, filed Feb. 4. 1997.

FIELD OF THE INVENTION

The present invention relates to novel bacterial genes and processes for improving the manufacture of clavams e.g. clavulanic acid. The present invention also provides novel organisms capable of producing increased amounts of clavulanic acid.

BACKGROUND OF THE INVENTION

Microorganisms, in particular Streptomyces sp. produce a number of antibiotics including clavulanic acid and other clavams, cephalosporins, polyketides, cephamycins, tumicamycin, holomycin and penicillins. There is considerable interest in being able to manipulate the absolute and relative amounts of these antibiotics produced by the microorganism and accordingly there have been a large number of studies investigating the metabolic and genetic mechanisms of the biosynthetic pathways (Domain, A. L. (1990) "Biosynthesis and regulation of beta-lactam antibiotics." In: 50 years of Penicillin applications, history and trends). Many of the enzymes which carry out the various steps in the metabolic pathways and the genes which code for these enzymes are known.

Clavams can be arbitrarily divided into two groups dependent on their ring stereochemistry (5S and 5R clavams). The biochemical pathways for the biosynthesis of 5R and 5S clavams have not yet been fully elucidated but it has been suggested that they are derived from the same starter units (an as yet unidentified 3 carbon compound (Townsend, C.A. and Ho, M. F. (1985) J. Am. Chem. Soc. 107 (4), 1066–1068 and Elson, S. W. and Oliver, R. S. (1978) J. Antibiotics XXXI No. 6. 568) and arginine (Velentine, B. P. et al (1993) J. Am Chem. Soc. 15, 1210–1211) and share some common imtermediates ([Iwata-Reuyl, D. and C. A. Townsend (1992) J. Am. Chem. Soc. 114: 2762–63, and lane, J. W. et al (1993) Bioorg. Med Chem. lett 3:2313–16).

Examples of 5S clavams include clavarn-2-carboxylate (C2C), 2-hydroxymethylclavam (2HMC), 2(3-alanyl) clavam, valclavam and clavaminic acid (GB 1585661, Rohl, F. et al. Arch. Miorbiol. 147:315–320, U.S. Pat. No. 4,202, 819). There are, however, few examples of 5R clavams and by far the most well known is the beta lactamase inhibitor clavulanic acid which is produced by the fermentation of Streptomyces clavligerus. Clavulanic acid, in the form of potassium clavulanate is combined with the beta-lactam amoxycillin in the antibiotic AUGMENTIN (Trade Mark SmithKline Beecham). Because of this commercial interest, investigations into the understanding of clavam biosynthesis have concentrated on the biosynthesis of the 5R clavam, clavulanic acid, by S.clavuligerus. A number of enzymes and their genes associated with the biosynthesis of clavulanic acid have been identified and published, Examples of such publications include Hodgson, J. E. et al., Gene 166, 49–55 (1995), Aidop, K. A. et al., Gene 147, 41–46 (1994), Patadkar, A. S. et al., J. Bact 177(5), 1307–14 (1995). In contrast nothing is known about the biosynthesis and genetics of 5S clavams other than clavarninic acid which is a clavulanic acid precursor produced by the action of clavaminic acid synthase in the clavulanic acid biosynthetic pathway in S. clavuligerus.

Gene cloning experiments have identified that S. clavuligerus contains two clavaminic acid synthase isoenzymes, cas1 and cas2 (Marsh E. N. et al Biochemistry 31, 12648–57, (1992)) both of which can contribute to clavulanic acid production under certain nutritional conditions (Paradkar, A. S. et al., J. Bact. 177(5), 1307–14 (1995)). Clavaminic acid synthase activity has also been detected in other clavulanic acid producing microorganisms, ie. S. jumonjinensis (Vidal, C. M., ES 550549, (1987)) and S. katsurahamancus (Kitano, K. et al., JP 53-104796, (1978)) as well as S. antibiticos, a producer of the 5S clavam, valclavam (Baldwin, J. E. et al, Tetrahedron Letts. 35(17), 2783–86, (1994)). The later paper also reported S. antibioticos to have proclavarnic acid amidino hydrolase activity, another enzyme known to be involved in clavulanic acid biosynthesis. All other genes identified in S. clavuligerus as involved in clavulanic biosynthesis have been reported to be required for clavulanic acid biosynthesis (Hodgson, J. E. et al., Gene 166, 49–55 (1995), Aidoo, K. A. et al., Gene 147, 41–46 (1994)) and as yet none have been reported which are specific for the biosynthesis of 5S clavams.

BRIEF SUMMARY OF THE INVENTION

The present invention relates to novel bacterial genes, processes for improving the manufacture of clavams, and novel organisms capable of producing increased amounts of clavulanic acid.

BRIEF DESCRIPTION OF THE DRAWINGS

FIG. 1 shows the nucleotide sequence of the S. Clavuligerus chromosome including the flanking cas1 (SEQ ID NO. 1).

DETAILED DESCRIPTION OF THE INVENTION

We have now identified certain genes which are specific for the biosynthesis of 5S clavams as exemplified by C2C and 2HMC in S. clavuligerus. Accordingly the present invention provides DNA comprising one or more genes which are specific for 5S clavam biosynthesis in S. clavuligerus and which are not essential for 5R clavam (e.g. clavulanic acid) biosynthesis.

By "gene" as used herein we also include any regulatory region required for gene function or expression. In a preferred sect the DNA is as identified as FIG. 1 (SEQ ID NO: 1). Preferably the DNA comprises the nucleotide sequences indicated in FIG. 1 (SEQ ID NO: 1) designated as orfup3 (SEQ ID NO: 2), orfup2 (SEQ ID NO: 3), orfup1 (SEQ ID NO: 4), orfdwn1 (SEQ ID NO: 5), orfdwn2 (SEQ ID NO: 6) and orfdwn3 (SEQ ID NO: 7). The present invention also provides proteins coded by said DNA. The present invention also provides vectors comprising the DNA of the invention and hosts containing such vectors.

Surprisingly we found that when at least one of the genes according to the invention is defective the amount of clavulanic acid produced by the organism is increased. Accordingly the present invention also provides processes for increasing the amount of clavulanic acid produced by a suitable microorganism. In one aspect of the invention the genes identified can be manipulated to produce an organism capable of producing increased amounts of clavam, suitably clavulanic acid. The findings of the present work also allow an improved process for the identification of organisms with higher clavulanic acid production comprising a preliminary screening for organisms with low or no 5S clavam production (for example by hplc and/or clavam bioassay as described in the examples herein).

Suitably the 5S clavam genes of the present invention can be obtained by conventional cloning methods (such as PCR) based on the sequences provided herein. The function of the gene can be interfered with or eliminated/deleted by genetic techniques such as gene disruption [Aidoo, K. A. et al., (.1994), Gene, 147, 41–46]., random mutagenesis, site directed mutagenesis and antisense RNA In a further aspect of the invention there are provided plasmids containing one or more defective genes, preferably the plasmids pCEC060, pCEC061, pCEC056 and pCEC057. described below.

Suitably, the plasmids of the invention are used to transform an organism such as S. clavuligerus, e.g. strain ATCC 27064 (which corresponds to S. clavuligerus NRRL 3585). Suitable transformation methods can be found in relevant sources including Sambrook, J., Fritsch, E. F. and Maniatis, T. (1989), Molecular cloning: a laboratory manual, 2nd Ed., ColdSpring Harbor Laboratory, Cold Spring Harbor, N.Y.; Hopwood, D. A. et al. (1985), Genetic Manipulation of Streptomyces. A Cloning Manual, and Paradkar, A. S. and Jensen, S. E. (1995), J. Bacteriol. 177 (5): 1307–1314.

Strains of the species S. clavuligerus are used industrially to produce clavulanic acid (potassium clavulanate). Within the British and United States Pharmacopoeias for potassium clavulanate (British Pharmacopoeia 1993, Addendum 1994; p1362-3 and U.S. Pharmacopeia Official Monographs 1995, USP 23 NF18 p384-5) the amounts of the toxic 5S clavam, clavam-2-carboxylate, are specifically controlled.

Therefore in a further aspect of the invention there is provided an organism capable of producing high amounts of clavulanic acid but has been made unable to make C2C or capable of producing high amounts of clavulanic acid but able to make only low levels of C2C. Suitably the clavulanic acid producing organism contains one or more defective clavam genes, and is preferably the S. clavuligerus strain 56-1A, 56-3A, 57-2B, 57-1C, 60-1A, 60-2A, 60-3A, 61-1A, 61-2A, 61-3A, and 61-4A, described below. Such organisms are suitable for the production of clavulanic acid without the production of the 5S clavam, clavam-2-carboxylate or with significantly reduced production of clavam-2-carboxylate.

EXAMPLES

In the examples all methods are as in Sambrook, J., Fritsch, E. F. and Maniatis, T. (1989) Molecular Cloning A Laboratory Manual (2nd Edition), or Hopwood, D. A. et al. (1985) Genetic Manipulation of Streptomyces. A Cloning Manual, and Paradkar, A. S. and Jensen, S. E. (1995) J. Bacteriol. 177 (5): 1307–1314 unless otherwise stated.

I. DNA Sequencing of the Streptomyces clavuligerus Chromosome Upstream and Downstream of the Clavaminate Synthase Gene cas1

A. Isolation of cas1

To isolate chromosomal DNA fragments from Streptomyces clavuligerus NRRL 3585 encoding the gene for clavaminate synthase isozyme 1 (cas1) an oligonucleotide probe RMO1was synthesised based on nucleotide 9–44 of the previously sequenced cas1 gene (Marsh, E. N., Chang, M. D. T. and Towned, C. A. (1992) Biochemnistry 31: 12648–12657). Oligonucleotides were constructed using standard methods on an Applied Biosystems 391 DNA Synthesiser. The sequence of RMO1, a 36-mer, was synthesised in the antiparallel sense to that published by Marsh et al (1992, ibid) RMO1 was radiolabelled with $^{32}$P using standard techniques for end-labelling DNA oligonucleotides (Sambrook et al., 1989 ibid), and was used to screen a cosmid bank of Streptomyces clavuligerus genomic DNA by Southern hybridization as described by Stahl and Amann (In: Nucleic acid techniques in bacterial systematics. Ed. E. Stackebrandt and M. Goodfellow. Toronto: John Wiley and Sons, p. 205–248, 1991). The genomic bank of S. clavuligerus DNA, prepared in cosmid pLAFR3, was as described by Doran, J. L et al., (1990), J. Bacteriol. 172 (9),4909–4918.

Colony blots of the S. clavuligerus cosmid bank were incubated overnight with radiolabelled RMO1 at 60° C. in a solution consisting of 5×SSC, 5× Denhardt's solution, and 0.5% SDS (1×SSC 0.15 M NaCl+0.015 M Na$_3$citrate; 1× Denhardt's solution: 0.2% BSA, 0.02% Ficoll, and 0.02% PVP). The blots were then washed at 68° C for 30 minutes in a solution of 0.5×SSC+0.1% SDS. One cosmid clone, .10D7, was isolated that hybridised strongly to RMO1 and gave hybridization signals upon digestion with restriction endonucleases SacI and EcoRI that were consistent with hybridization signals detected in similar experiments with digests of S. clavuligerus genomic DNA.

B. DNA sequencing of the S. clavuligerus Chromosome Flanking cas1

A partial restriction map of cosmid 10D7 was generated using restriction endonucleases SacI, NcoI, and KpnI. Southern hybridization experiments between RMO1and various digests of 10D7 DNA indicated that cas1 was most likely located at one end of a 7-kb SacI-SacI DNA subfragment. This fragment consisted of the cas1 open reading frame and approximately 6 kb of upstream DNA. The 7-kb fragment was then subcloned from a SacI digest of 10D7 in the phagemid vector pBluescriptII SK+ (2.96 kb; Stratagene), thus generating the recombinant plasmid pCEC007.

To facilitate the process of sequencing the chromosome upstream of cas1, a 3-kb NcoI—NcoI subfragment of the 7-kb SacI-SacI fragment was subcloned in pUC120 (3.2 kb; Vieirra and Messing, Methods Enzymoi. 153, 3–11, 1987)) in both orientations, generating the recombinant plasmids pCEC026 and pCEC027. The 3-kb subfragment consisted of the amino-terminal-encoding portion of cas1 and approximately 2.6 kb of upstream DNA.

Nested, overlapping deletions were created in both pCEC026 and pCEC027 using exonuclease III and S1 nuclease digestion (Sambrook et al., 1989 ibid) and the DNA sequence of the 3-kb NcoI—NcoI fragment was determined on both strands by the dideoxy chain termination method (Sanger, F., Nicklen, S. and Coulson, A. R. (1977), Proc. Natl. Acad. Sci. U.S.A. 74: 5463–5467) using a Taq dye-deoxy$^a$ terminator kit and an Applied Biosystems 373A Sequencer.

To determine the DNA sequence of the chromosome immediately downstream of cas1 a 4.3-kb KpnI-EcoRI DNA fragment was subcloned from cosmid clone 10D7 in pBluescriptII SK+, generating pCEC018. From pCEC018 a 3.7-kb SacI—SacI subfragment was cloned in pSL1180 (3.422 kb, Pharnacia); one of the SacI termini of this fragment partially overlapped the TGA stop codon of cas1, the other was vector encoded. Both orientations of the 3.7-kb fragment were obtained during subcloning and the resulting recombinant plasmids were designated pCEC023 and pCEC024. Nested, overlapping deletions were created in both plasmids and the DNA sequence of the 3.7-kb fragment was determined on both strands. The nucleotide sequence of the *S. clavuligerus* chromosome generated in these experiments, including and flanking cas1 sequence is shown in FIG. 1.

II. Functional Analysis of the Open Reading Frames Flanking cas1

Computer analysis of the DNA sequence upstream of casl predicted the presence of two complete orfs and one incomplete orf. All three orfs were located on the opposite DNA strand to casl and were thus oriented in the opposite direction. The first open reading frame, orfup1, was located 579 bp upstream of cas1 and encoded a polypeptide of 344 amino acids (aa). The second open reading frame, orfup2, was located at 437 bp beyond the 3'-end of orfup1 and encoded a 151 aa polypeptide. Beyond orfup2 is orfup3. The start codon of orfup3 overlaps the translational stop codon of orfup2, suggesting that the two orfs are translationally coupled. No translational stop codon for orfup3 as located on the 3-kb NcoI—NcoI fragment.

A similar analysis of the DNA sequence downstream of cas1 predicted the presence of two complete orfs and one incomplete orf. Two of the orfs were located on the opposite DNA strand to cas1 and were thus oriented towards casl. The third orf was located on the same strand as cas1 and was thus oriented away from it. The first downstream open reading frame, orfdwn1, was located 373 bp downstream of cas1 and encoded a 328 aa polypeptide. The second open reading frame, orfdwn2, was located 55 bp upstream of orfdwn1 and encoded a 394 aa polypeptide. At 315 bp upstream of orfdwn2 and on the opposite strand was orfdwn3. Because no stop codon was observed for orfdwn3 on the 3.7-kb fragment, it encoded an incomplete polypeptide of 219 aa.

Gene Disruption of the orfup and orfdwn Open Reading Frames

To assess the possible roles of the open reading frames flanking cas1 in the biosynthesis of clavulanic acid and the other clavams produced by *S. clavuligerus*, insertional inactivation or deletion mutants were created by gene replacement The method used for gene disruption and replacement was essentially as described by Paradkar and Jensen (1995 ibid).

A. orfup1

1.5-kb NcoI—NcoI fragment carrying the apramycin resistance gene (apr$^r$), constructed as described in Paradkar and Jensen (1995 ibid), was treated with Klenow fragment to generate blunted termini (Sambrook et al., 1989 ibid) and was ligated to pCEC026 that had been digested with BsaBI and likewise treated with Klenow fragment. pCEC026 possesses a BsaBI site located within orfup1 at 636 bp from the translational start codon. The ligation mixture was used to transform competent cells of *E. coli* GM 2163 (available from New England Biolabs, USA., Marinus, M. G. et al M G G (1983) vol 122, p288–9) to apramycin resistance. From the resulting transformants two clones containing plasmids pCEC054 and pCEC055 were isolated; by restriction analysis pCEC054 was found to possess the apr$^r$-fragment inserted in the same orientation as orfup1, while pCEC055 possessed it in the opposite orientation.

To introduce pCEC054 into *S. clavuligerus*, plasmid DNA was digested with BamHI and HindIII and ligated to the high-copy number Streptomyces vector pU486 (6.2 kb; Ward et al., (1986) Mol. Gen. Genet. 203: 468–478). The ligation mixture was then used to transform *E. coli* GM2163 competent cells to apramycin resistance. From the resulting transformants one clone, possessing the shuttle plasmid pCEC061, was isolated. This plasmid was then used to transform *S. clavuligerus* NRRL 3585. The resulting transformants were put through two successive rounds of sporulation on non-selective media and then replica plated to antibiotic containing media to identify apramycin-resistant and thiostrepton-sensitive transformants. From this process four putative mutants (61-1A, -2A, -3A and 4A) were chosen for further analysis.

To confirm that these putative mutants were disrupted in orfup1 genomic DNA was prepared from isolates 61-1A and 61-2A, digested with SacI and subjected to Southern blot analysis. The results of the Southern blot were consistent with a double cross-over having occurred and demonstrated that these mutants are true disruption replacement mutants in orfup1.

The mutants 61-1A, -2A, -3A and -4A were grown in Soya-Flour medium and their culture supernatants were assayed by HPLC for clavulanic acid and clavam production. The composition of the Soya-Flour medium and the method for assaying clavams by HPLC were as previously reported (Paradkar and Jensen, 1995 ibid) except that the running buffer for the HPLC assay consisted of 0.1 M NaH$_2$PO$_4$+6% methanol, pH 3.68 (adjusted with glacial acetic acid). The HPLC analysis indicated that none of the mutants produced detectable levels of clavam-2-carboxylate or 2-hydroxymethylclavam. Furthermore, when culture supernatants were bioassayed against Bacillus sp. ATCC 27860, using the method of Pruess and Kellett (1983, J. Antibiot. A: 208–212)., none of the mutants produced detectable levels of alanylclavam. In contrast, HPLC assays of the culture supernatants showed that the mutants appeared to produce superior levels of clavulanic acid when compared to the wild-type (Table 1).

TABLE 1

Clavulanic acid titre (CA) of orfup1 mutants in shake flask tests

| STRAIN | 70 HOURS CA ug/ml | 70 HOURS CA ug/mg DNA | 93 HOURS CA ug/ml | 93 HOURS CA ug/mg DNA |
|---|---|---|---|---|
| NRRL 3585 #1 | 87 | 915 | 166 | 1963 |
| NRRL 3585 #2 | 66 | 790 | 159 | 1842 |
| 61-1A | 272 | 2894 | 439 | 6113 |
| 61-2A | 199 | 2148 | 225 | 2928 |
| 61-3A | 54 | 692 | 221 | 2585 |
| 61-4A | 0 | 0 | 226 | 2422 |

B. orfdwn1 and orfdwn2

A deletion/replacement mutant in orfdwn1 and orfdwn2 was created by first digesting pCEC018 (7.3 kb) with NcoI and liberating a 1-kb subfragment containing most of orfdwn1 and a portion of orfdwn2. The digest was fractionated by agarose-gel electrophoresis and the 6.3-kb fragment was excised and eluted from the gel. This fragment was then ligated to an NcoI—NcoI DNA fragment carrying apr$^r$ and used to transform *E. coli* XL1-Blue to apramycin resistance. One clone was obtained from this experiment but restriction analysis of the resulting recombinant plasmid revealed that two copies of the apramycin resistance fragment had been ligated into the deletion plasmid. To eliminate the extra copy of the apr$^r$-fragment, the plasmid was digested with NcoI and self-ligated. The ligation mixture was used to transform *E. coli* GM2163 to apramycin resistance. From the transformants, two clones were isolated that contained plasmids pCEC052 and pCEC053 both of which possessed only one copy of the apr$^r$-fragment; pCEC052 possessed the apr$^r$-fragment inversely oriented with respect to orfdwn1 and 2, while pCEC053 possessed the apr$^r$-fragment inserted in the same orientation as orfdwn1 and 2.

A shuttle plasmid of pCEC052 was constructed by ligating BamHI-digested pCEC052 with similarly digested pIJ486 and transforming *E. coli* GM2163 to apranycin resistance. From this experiment one clone was isolated that contained the shuttle plasmid pCEC060. This plasmnid was used to transform wild-type *S. clavuligerus* 3585to apramycin and thiostrepton resistance. The resulting transformants were put through two rounds of sporulation under non-selective conditions and then replica plated to antibiotic containing media to identify apramycin resistant, thiostrepton sensitive colonies. Three putative mutants (60-1A, -2A and -3A) were chosen for further analysis.

To establish the identity of these putative mutants genomic DNA was isolated from strains 60-1A and 60-2A and digested with either SacI or BstEII and subjected to southern blot analysis. The hybridisation bands generated from this experiment were consistent with both strains having undergone a double cross-over event demonstrating that these mutants are true disruption replacement mutants in orfdwn1/2.

When these were cultured in Soya-Flour medium and their culture supernatants assayed by HPLC, none of the mutants produced detectable levels of clavam-2-carboxylate or 2-hydroxymethylclavam A bioassay of the culture supernatants showed that the mutants also failed to produce detectable levels of alanylclavam. As with the orfup1 mutants,the orfdwn1/2 mutants are capable of producing superior to wild-type levels of clavulanic acid (Table2).

TABLE 2

Clavulanic acid titre (CA) orfdwn1/2 mutants in shake flask tests

| STRAIN | 70 HOURS CA ug/ml | 70 HOURS CA ug/mg DNA | 93 HOURS CA ug/ml | 93 HOURS CA ug/mg DNA |
|---|---|---|---|---|
| NRRL 3585 #1 | 87 | 915 | 166 | 1963 |
| NRRL 3585 #2 | 66 | 790 | 159 | 1842 |
| 60-1A | 164 | 1872 | 260 | 2911 |
| 60-2A | 187 | 2013 | 108 | 1320 |
| 60-3A | 79 | 994 | 214 | 2161 | orfdwn3

To disrupt orfdwn3 pCEC023 (consisting of a 3.7-kb fragment of casl downstream DNA subcloned into pSL1180) was digested with NcoI and then self ligated. After transforming *E.coli* with the ligation mixture a clone was isolated that possessed the plasmid pCEC031. This plasmid retained only the 1.9kb NcoI-EcoRI fragment encoding a portion of orfdwn2 and the incomplete orfdwn3. An examination of the DNA sequence revealed that pCEC031 possessed a unique BstEII site at 158bp from the translational start site of orfdwn3. Therefore, pCEC031 was digested with BstEII, treated with Klenow fragment to create blunt ends and then ligated to a blunted apramycin resistance cassette. The ligation mixture was used to transform *E.coli* GM2163 to apramycin resistance and ampicillin resistance. Two transformants were selected that contained respectively pCEC050 and pCEC051 restriction analysis revealed that the apramycin resistance cassette was orientated in the same orientation as orfdwn3 in pCEC050 and in the opposite orientation in pCEC051. Both of these plasmids were then digested with HindIII and ligated to similarly digested pU486. The ligation mixtures were then used separately to transform *E.coli* GM 2163 to apramycin and ampicillin resistance. The shuttle plasmids pCEC056 (pCEC050+pIJ486) and pCEC057 (pCEC051+pLI486) were isolated from the resultant transformants. Both plasmids were then used to transform *S.clavuligerus* NRRL 3585.

One transformant was selected from each transformant experiment and put through two successive rounds of sporulation on non-selective media and then replica plated to antibiotic containing media to identify apramycin-resistant and thiostrepton-sensitive transformants. From this process two putative mutants from the progeny of each primary transformant. (56-1A and 56-3A for pCEC056, and 57-1C and 57-2B for pCEC057).

To establish the identity of these putative mutants genomic DNA was isolated from these strains and digested with either SacI or Acc65I and subjected to Southern blot analysis. The hybridisation bands generated from this experiment were consistent with both strains having undergone a double cross-over event demonstrating that these mutants are true disruption replacement mutants in orfdwn3.

When these strains were cultured in Soya-Flour medium and their culture supernatants assayed by HPLC, the mutants produced greatly reduced levels of clavam-2-carboxylate or 2-hydroxymethylclavam. A bioassay of the culture supernatants showed that the mutants also failed to produce detectable levels of alanylclavam. As with the orfup1 and orfdwn1/2 mutants, the orfdwn3 mutants were capable of producing superior to wild-type levels of clavulanic acid (Table 3).

TABLE 3

Clavulanic acid titre (CA) orfdwn3 mutants in shake flask tests

| STRAIN | 71 HOURS CA ug/ml | 71 HOURS CA ug/mg DNA | 93 HOURS CA ug/ml | 93 HOURS CA ug/mg DNA |
|---|---|---|---|---|
| NRRL 3585 #1A | 180 | 1580 | 193 | 1790 |
| NRRL 3585 #1B | 179 | 1640 | 266 | 2310 |
| 56-1A | 34 | 110 | 235 | 2160 |
| 56-3A | 225 | 2140 | 274 | 2740 |
| 57-1C | 253 | 2910 | 277 | 2920 |
| 57-2B | 242 | 2240 | 193 | 1860 |

The application discloses the following nucleotide sequences:
SEQ ID No. 1: DNA sequence of FIG.1
SEQ ID No. 2: orfup3 sequence
SEQ ID No. 3: orfup2 sequence
SEQ ID No. 4: orfup1 sequence
SEQ ID No. 5: orfdwn1 sequence
SEQ ID No. 6: orfdwn2 sequence
SEQ ID No. 7: orfdwn3 sequence

What is claimed is:

1. An isolated DNA comprising one or more genes essential for clavam-2carboxylate (C2C), 2-hydroxymethylclavam (2HMC), or 2-(3-alanyl)clavam (AC) biosyithesis in *S. clavuligerus*, wherein said one or more genes is not essential for clavulanic acid biosynthesis; wherein said one or more genes include an open reading frame selected from the group consisting of: SEQ ID NO:4, SEQ ID NO:5, SEQ ID NO:6 and SEQ ID NO:7.

2. The DNA according to claim 1 comprising the sequence of SEQ ID NO:1.

3. The DNA according to claim 1 comprising the sequence of SEQ ID NO:4.

4. An isolated DNA which hybridizes with the DNA of claim 1,
wherein said hybridization is performed overnight at 60° C. in a solution consisting of 5×SSC, 5× Denhardt's solution and 0.5% SDS (1×SSC: 0.15M NaCl+0.015M Na₃citrate; 1× Denhardt's solution: 0.02% BSA, 0.02% Ficoll and 0.02%PVP), and washed at 680° C. for 30 minutes in a solution of 0.5% SSC+0.1% SDS;
wherein said isolated DNA comprises one or more genes essential for clavam-2-carboxylate (C2C), 2-hydroxymethylclavam (2HMC), or 2-(3-alanyl) clavam (AC) clavam biosynthesis; and
wherein said genes are not essential for clavulanic acid biosynthesis.

5. A vector comprising the DNA of claim 1.

6. A Streptomyces host containing the vector of claim 5.

7. A Streptomyces host according to claim 6 which is *S. clavuligerus*.

8. A vector comprising the DNA of claim 4.

9. A Streptomyces host comprising the vector of claim 8.

10. A Streptomyces host according to claim 9 which is *S. clavuligerus*.

11. An isolated DNA comprising at least one open reading frame selected from the group consisting of: SEQ ID NO:4, SEQ ID NO:5, SEQ ID NO:6 and SEQ ID NO:7 wherein at least one said open reading frame is interfered with such that when at least one corresponding endogenous open reading frame in *Streptomyces clavuligerus* genome is replaced by at least one said interfered with open reading frame the levels of clavam-2-carboxylate (C2C), 2-hydroxymethylclavam (2HMC), or 2-(3-alanyl)clavam (AC) produced by said *Streptomyces clavuligerus* are reduced or eliminated.

12. A vector comprising the isolated DNA of claim 11.

13. An *Streptomyces clavuligerus* comprising the isolated DNA of claim 11.

14. *Streptomyces clavuligerus* having reduced or eliminated clavam-2-carboxylate (C2C), 2-hydroxymethylcla-vam (2HMC), or 2-(3-alanyl)clavam (AC) biosynthesis wherein at least one open reading frame essential for clavam-2-carboxylate (C2C). 2-hydroxymethylclavam (2HMC), or 2-(3-alanyl)clavam (AC) biosynthesis, but not essential for clavulanic acid biosynthesis, selected from the group consisting of: orfup1 (SEQ ID NO:4), orfdwn 1 (SEQ ID NO:5), orfdwn2 (SEQ ID NO:6) and orfdwn3 (SEQ ID NO:7) is interfered with or eliminated by a genetic technique selected from the group consisting of: gene disruption, random mutagenesis, and site-directed mutagenesis, and wherein clavam-2-carboxylate (C2C), 2-hydroxymethylclavam (2HMC), or 2-(3-alanyl clavam (AC) biosynthesis in said *Streptomyces clavuligerus* is reduced or eliminated and clavulanic acid production is maintained or increased relative to clavulanic acid production from *S. clavuligerus* strain ATCC 27064.

15. The *S. clavuligerus* of claim 14, wherein the open reading frame is orfup1 (SEQ ID NO:4).

16. The *S. clavuligerus* of claim 14, wherein the open reading frame is orfdwn1 (SEQ ID NO:5).

17. The *S. clavuligerus* of claim 14, wherein the open reading frame is orfdwn2 (SEQ ID NO:6).

18. The *S. clavuligerus* of claim 14, wherein the open reading frame is orfdwn3 (SEQ ID NO:7).

19. The *S. clavuligerus* of claim 14, wherein the biosynthesis of clavam-2-carboxylate (C2C) is reduced or eliminated.

20. The *S. clavuligerus* of claim 14, wherein the biosynthesis of 2-hydroxymethylclavam (2HMC) is reduced or eliminated.

21. The *S. clavuligerus* of claim 14, wherein the biosynthesis of 2-(3-alanyl)clavam (AC) is reduced or eliminated.

22. *Streptomyces clavuligerus* wherein a portion of at least one open reading from selected from the group consisting of: orfup1 (SEQ ID NO:4), orfdwn 1 (SEQ ID NO:5), orfdwn2 (SEQ ID NO:6) and orfdwn3 (SEQ ID NO:7) is deleted from the genome of said *Streptomyces clavuligerus* and wherein clavam-2-carboxylate (C2C), 2-hydroxymethylclavam (2HMC), or 2-(3-alanyl)clavam (AC) biosynthesis by said *Streptomyces clavuligerus* is reduced or eliminated and clavulanic acid production by said *Streptomyces clavuligerus* is maintained or increased relative to clavulanic acid production from *S. clavuligerus* strain ATCC 27064.

23. The *Streptomyces clavuligerus* of claim 22 wherein the portion of said at least one open reading frame that is deleted from said genome comprises at least one entire open reading frame.

* * * * *

UNITED STATES PATENT AND TRADEMARK OFFICE
CERTIFICATE OF CORRECTION

PATENT NO. : 6,936,458 B1 Page 1 of 1
APPLICATION NO. : 09/350702
DATED : August 28, 2001
INVENTOR(S) : Cecilia Anders et al.

It is certified that error appears in the above-identified patent and that said Letters Patent is hereby corrected as shown below:

At column 35, line 18 please change "biosyithesis" with --biosynthesis--

At column 35, line 33 please change "680° C" to --68 C--

At column 15, line 16, please replace the period after "clavam-2-carboxylate (C2C)" with a comma Signed and Sealed this First Day of May, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,936,458 B1 |
| APPLICATION NO. | : 09/350702 |
| DATED | : August 30, 2005 |
| INVENTOR(S) | : Cecilia Anders et al. |

It is certified that error appears in the above-identified patent and that said Letters Patent is hereby corrected as shown below:

At column 35, line 18 please change "biosyithesis" with --biosynthesis--

At column 35, line 33 please change "680° C" to --68 C--

At column 15, line 16, please replace the period after "clavam-2-carboxylate (C2C)" with a comma This certificate supersedes Certificate of Correction issued May 1, 2007.

Signed and Sealed this

Twenty-second Day of May, 2007

JON W. DUDAS
*Director of the United States Patent and Trademark Office*